United States Patent [19]
Levy

[11] Patent Number: 5,902,596
[45] Date of Patent: May 11, 1999

[54] CONTROLLED DELIVERY COMPOSITIONS AND PROCESSES FOR TREATING ORGANISMS IN A COLUMN OF WATER OR ON LAND

[75] Inventor: Richard Levy, Fort Myers, Fla.

[73] Assignee: Lee County Mosquito Control District, Fla.

[21] Appl. No.: 08/921,574

[22] Filed: Sep. 29, 1997

Related U.S. Application Data

[60] Division of application No. 08/434,313, May 2, 1995, Pat. No. 5,698,210, which is a continuation-in-part of application No. 08/409,301, Mar. 24, 1995, abandoned, which is a continuation-in-part of application No. 08/406,344, Mar. 17, 1995, abandoned.

[51] Int. Cl.$^6$ .................................................. A01N 25/10
[52] U.S. Cl. .......................... 424/405; 424/406; 424/408; 424/409; 424/417; 424/418; 424/419; 424/420; 424/421; 424/485; 424/486; 424/487; 424/488; 424/489; 424/93.1
[58] Field of Search ................................ 524/154, 58, 26; 424/405–409, 417–421, 485–489, 93.1, 93.461

[56] References Cited

U.S. PATENT DOCUMENTS

| | | | |
|---|---|---|---|
| 3,274,052 | 9/1966 | Yaffe et al. | 167/42 |
| 3,917,814 | 11/1975 | Hedges et al. | 424/43 |
| 4,464,317 | 8/1984 | Thies et al. | 264/4.3 |
| 4,818,534 | 4/1989 | Levy | 424/404 |
| 4,983,389 | 1/1991 | Levy | 424/404 |
| 4,983,390 | 1/1991 | Levy | 424/404 |
| 4,985,251 | 1/1991 | Levy | 424/404 |
| 5,180,585 | 1/1993 | Jacobson et al. | 424/405 |
| 5,273,749 | 12/1993 | Bok et al. | 424/405 |

*Primary Examiner*—Neil S. Levy
*Attorney, Agent, or Firm*—Finnegan, Henderson, Farabow, Garrett & Dunner, L.L.P.

[57] ABSTRACT

Controlled release compositions of matter are disclosed comprising complexes for treating a population of one or more aquatic organisms in a column of water. The complexes comprise at least one system wherein the system comprises at least one bioactive agent as a component selected for treating a population of aquatic organisms, at least one carrier component, and at least one coating component for regulating the controlled release rate and release profile of the bioactive agent in water or at least one bioactive agent and one joint-function component that can serve as both a carrier and coating to regulate the controlled release rate and release profile of the bioactive agent in water, with or without optional binder components and/or additional formulation materials. The components are selected to sink or float so that the complexes will permeate and/or remain in any planar or volumetric segment of a water column for a period of time that is sufficient to effectively treat a population of aquatic organisms. Methods for treating a column of water are also disclosed which comprises delivering the compositions to a column of water or to a dry preflood area (pretreatment) that will develop in a column of water or a flood area. The composition and process can also be used to treat terrestrial organisms.

32 Claims, 1 Drawing Sheet

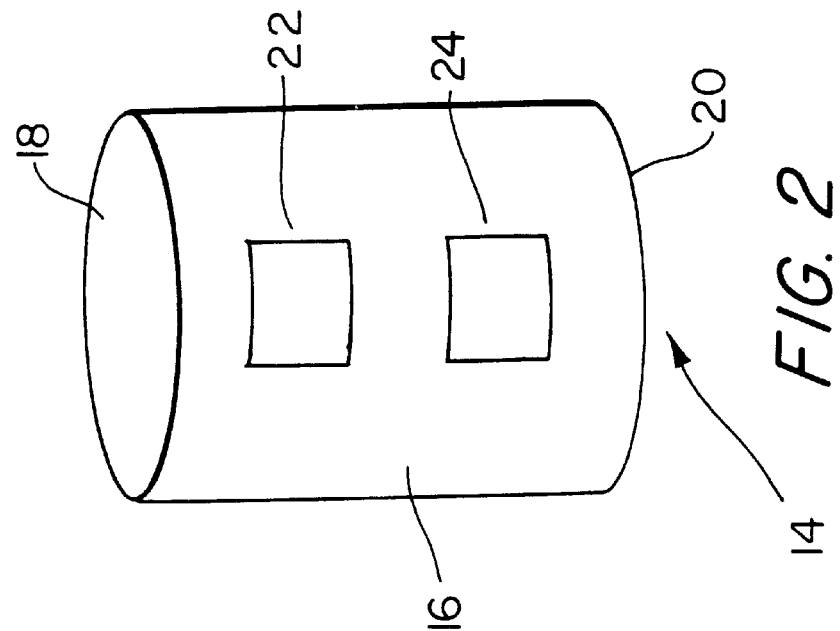
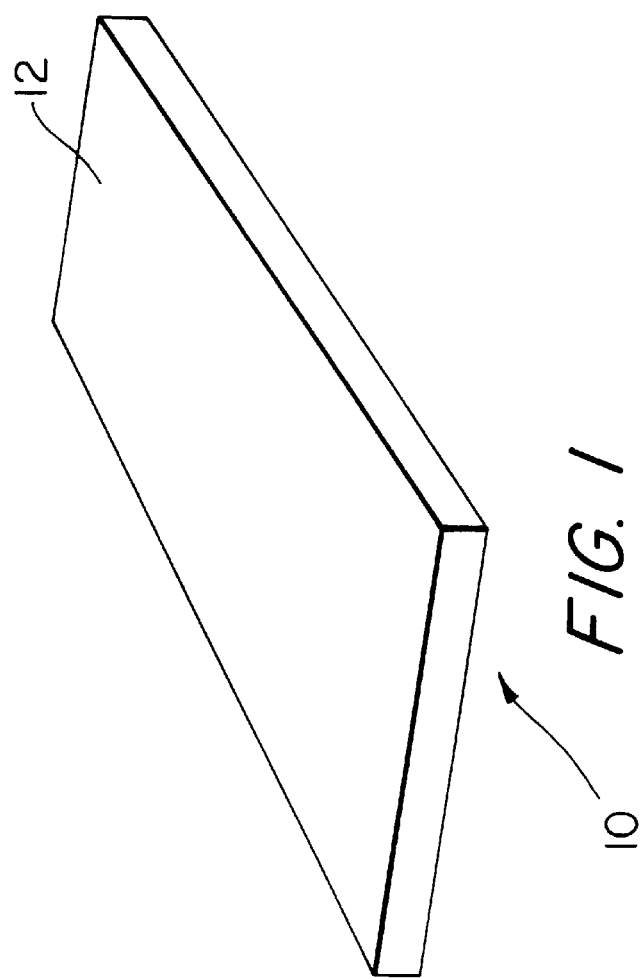

CONTROLLED DELIVERY COMPOSITIONS AND PROCESSES FOR TREATING ORGANISMS IN A COLUMN OF WATER OR ON LAND

This is a division of application Ser. No. 08/434,313, U.S. Pat. No. 5,698,210 as originally filed on May 2, 1995 which is a CIP application of application, now abandoned, of Ser. No. 08/409,301 filed on Mar. 24, 1995, which is a CIP application, now abandoned of Ser. No. 08/406,344 filed on Mar. 17, 1995 all of which are incorporated herein by reference.

BACKGROUND OF THE INVENTION

1. Field of Invention

The present invention is directed to compositions and processes for controlled delivery of bioactive agents to a population of aquatic organisms located in any planar or volumetric segment of a column of water by ground or aerial application techniques. Organisms of special interest are disease-carrying or biting or non-biting nuisance insects, and parasitic animals or plants, especially weeds. Compositins for controlled delivery of bioactive agents to terrestrial organisms are also described.

2. Description of Related Art

Various methods have been devised for delivering biologically active materials to control pests and vegetation. For example, Yaffe et al., U.S. Pat. No. 3,274,052 describes a process and a composition in which molten droplets of a normally solid toxicant are sprayed on the surface of a granular carrier whereupon they adhere to and solidify on the surface of the carrier as an adherent coating. When employed for treating aquatic environments, the specific gravity of the granules, and the rate of release of the toxicant is adjusted during the manufacture to provide surface, intermediate or bottom contact, or penetration into mud to control the specific organisms involved. Neither methods nor compositions are described for adjusting the specific gravity.

Hedges et al., U.S. Pat. No. 3,917,814, describes a non-poisonous insecticidal composition consisting of diatomaceous earth having a sorptive silica gel adhered to the surface.

Jacobson et al., U.S. Pat. No. 5,180,585, describes an antimicrobial composition consisting of inorganic core particles coated with a metal or metal compound having antimicrobial properties.

Thies et al., U.S. Pat. No. 4,464,317, describes a process for encapsulating a pesticide with an inorganic silicate coating. The encapsulated materials according to the inventors are capable of fragmenting upon storage in water to provide controlled release of a pesticide such as a mosquito control agent. Non-encapsulated materials were shown to have about half the active life of the encapsulated materials.

Levy, U.S. Pat. Nos. 4,818,534; 4,983,389; 4,983,390; and 4,985,251, describe various insecticidal, herbicidal, terrestrial, and flowable insecticidal delivery compositions based on bioactive materials and superabsorbent polymers.

One of the problems encountered in delivering bioactive materials to aquatic environments is that the aquatic organism to be treated is not immediately susceptible to being contacted with the bioactive material because of its location in a column of water either at the surface, the bottom, or some intermediate region in between. Because of the specific gravity of the bioactive material, in many instances it cannot be targeted to precisely treat the organisms of interest in the water column. By way of example, bioactive materials that have a specific gravity greater than water will generally be ineffective for treating aquatic organisms at the surface of a column, and vice-versa. Aquatic organisms that persist at some intermediate level are also difficult to treat for the same reason.

The foregoing illustrates that various delivery systems have been devised for bioactive materials, and the need to have a controlled delivery system suitable for delivering these materials to aquatic organisms. Although there is some suggestion that by adjusting the specific gravity of a toxicant composition of matter, it would be suitable for delivering the toxicant to an aquatic environment either at the surface, the bottom or at some intermediate level, the means for adjusting the specific gravity have not been disclosed.

Accordingly, the present invention is directed to compositions and processes for treating a population of one or more aquatic organisms in a column of water in which the foregoing and other disadvantages are overcome.

The present invention is also directed to compositions and processes for pretreating a dry (preaquatic) habitat area before it has been flooded by rain or tides, and which is a breeding site for the target aquatic organism(s), i.e. a pre-flood area. Pretreating a flooded aquatic habitat area before the target aquatic organism(s) breed is also within the scope of the invention, as well as flooded habitats where the organisms exist.

The foregoing illustrates that various delivery systems have been devised for bioactive materials, and the need to have a controlled delivery system suitable for delivering these materials to one or more terrestrial organisms, i.e. non-aquatic organisms. Although there are some systems that are available to provide control of these organisms, it would be advantageous to provide additional compositions for addressing the problems caused by such organisms whether they are plant, insect, or other animal pests.

Accordingly, the present invention is directed to compositions and processes for treating one or more terrestrial organisms in which the foregoing and other disadvantages are overcome.

Specifically, the advantages sought to be obtained according to the present invention are to provide compositions of matter or processes for treating a population of one or more aquatic organisms in a column of water, or one or more terrestrial organisms. Throughout the specification it is intended that the terms "treat," "treating," or "treatment" are intended to mean enhancing development of an organism, prolonging life of an organism, stopping or reversing the development of a condition in an organism, stopping the development of an organism, or eradicating an organism.

SUMMARY OF INVENTION

These and other advantages are realized by the present invention which comprises compositions of matter and processes which substantially obviates one or more of the limitations and disadvantages of the related art.

Additional features and advantages of the invention will be set forth in the written description which follows, and in part will be apparent from this description, or may be learned by practice of the invention. The objectives and other advantages of the invention will be realized and attained by the compositions of matter and processes particularly pointed out in the written description and claims hereof.

To achieve these and other advantages, and in accordance with the purpose of the invention, as embodied and broadly described, the invention comprises compositions of matter for treating an aquatic column of water comprising a bioactive agent as a component for treating a population of one or more aquatic organisms, a carrier component, and a coating component for regulating the controlled release rate (i.e. fast, slow, pulsed or delayed), and release profile (i.e. zero-order, first-order, and square-root-of-time kinetics) of the bioactive agent in water. The compositions of matter of the invention can optionally be combined with a binder component to aid in agglomerating the compositions, or a variety of formulation ingredients to enhance the performance of the compositions.

Compositions of matter are also described for treating a population of one or more aquatic organisms in a column of water comprising a bioactive agent as a component for treating a population of one or more aquatic organisms, and a joint-function carrier component that not only carries the bioactive material but also is a coating component for regulating the controlled release rate, and release profile of the bioactive agent in water. The compositions of matter of the invention can optionally be combined with a binder component to aid in agglomerating the compositions, or a variety of formulation ingredients to enhance the performance of the compositions.

Further in this regard, a composition of matter is provided comprising a complex for treating a population of one or more aquatic organisms in a column of water, the complex comprising at least one controlled delivery system wherein the controlled delivery system comprises at least one bioactive agent as a component for treating a population of one or more aquatic organisms, at least one carrier component, at least one coating component for regulating the controlled release rate, and release profile of the bioactive agent in water, with or without one or more binder component(s) for agglomerating said composition into larger units such as granules, pellets, and briquets, or additional formulation ingredients.

In another complex, the controlled delivery system comprises at least one bioactive agent as a component for treating a population of aquatic organisms, at least one joint-function carrier component that is also a coating component for regulating the controlled release rate, and release profile of the bioactive agent in water, with or without one or more binder components for agglomerating said composition into larger units such as granules, pellets, and briquets, or additional formulation ingredients.

In yet another complex, the controlled delivery system comprises at least one bioactive agent as a component for treating a population of one or more aquatic organisms, at least one joint-function carrier component that is also a coating component for regulating the controlled release rate, and release profile of the bioactive agent in water, at least one additional component such as an additional coating component to further regulate or modify the controlled release rate, and release profile of the bioactive agent in water, with or without one or more binder components for agglomerating said composition into larger units such as granules, pellets, and briquets, or additional formulation ingredients.

The components are selected to sink or float so that each complex or composition will permeate, and remain in any planar or volumetric segment of a water column for a period of time sufficient to effectively treat a population of one or more aquatic organisms.

A method is also provided in which the foregoing compositions are delivered to the column of water in order to time-release the bioactive agent(s) in the water so as to make it available to treat the aquatic organisms.

The invention also comprises compositions of matter for treating one or more terrestrial organisms comprising a bioactive agent as a component for treating a population of one or more terrestrial organisms, a carrier component, and a coating component for regulating the controlled release rate, and release profile of the bioactive agent. These compositions of matter of the invention can optionally be combined with a binder component to aid in agglomerating the compositions, or a variety of formulation ingredients to enhance the performance of the compositions.

Compositions of matter are also described for treating a population of one or more terrestrial organisms comprising a bioactive agent as a component for treating a terrestrial organism, and a joint-function carrier component that not only carries the bioactive material but also is a coating component for regulating the controlled release rate, and release profile of the bioactive agent. The compositions of matter of the invention can optionally be combined with a binder component to aid in agglomerating the compositions, or a variety of formulation ingredients to enhance the performance of the compositions.

Further in this regard, a composition of matter is provided comprising a complex for treating a population of one or more terrestrial organisms, the complex comprising at least one controlled delivery system wherein the controlled delivery system comprises at least one bioactive agent as a component for treating a terrestrial organism, at least one carrier component, at least one coating component for regulating the controlled release rate, and release profile of the bioactive agent, with or without one or more binder component(s) for agglomerating said composition into larger units such as granules, pellets, and briquets, or additional formulation ingredients.

In another complex, the controlled delivery system comprises at least one bioactive agent as a component for treating a population of one or more terrestrial organisms, at least one joint-function carrier component that is also a coating component for regulating the controlled release rate, and release profile of the bioactive agent, with or without one or more binder components for agglomerating said composition into larger units such as granules, pellets, and briquets, or additional formulation ingredients.

In yet another complex, the controlled delivery system comprises at least-one bioactive agent as a component for treating a population of one or more terrestrial organisms, at least one joint-function carrier component that is also a coating component for regulating the controlled release rate, and release profile of the bioactive agent, at least one additional component such as an additional coating component to further regulate or modify the controlled release rate, and release profile of the bioactive agent, with or without one or more binder components for agglomerating said composition into larger units such as granules, pellets, and briquets, or additional formulation ingredients.

A method is also provided in which the foregoing compositions are delivered to a terrestrial environment in order to time-release the bioactive agent(s) so as to make it available to treat the terrrestrial organisms. The terrestrial environment is one that is a habitat or potential habitat for the terrestrial organisms.

It is understood that both the foregoing general description and the following detailed description are exemplary, and explanatory, and further, the following description is intended to provide a more detailed explanation of the invention as claimed.

BRIEF DESCRIPTION OF THE DRAWINGS

FIG. 1 is a perspective view of a degradable container, such as a water soluble polyvinyl alcohol pouch containing the composition of the present invention; and FIG. 2 is a perspective view of a dispensing container having apertures for dispensing the composition of the present invention to an aquatic or terrestrial habitat.

DETAILED DESCRIPTION

The effectiveness of bioactive materials, especially on aquatic organisms, is generally dependent on delivery of the material to the specific organisms that are targeted for treatment, i.e., effectiveness is dependent on the bioavailability of the material which can be problematic in aqueous environments. For example, some bioactive materials when delivered to an aqueous environment will not remain in the region of interest, where the aquatic organisms are located, for a length of time sufficient to provide complete treatment of the organism. This is generally remedied by several successive treatments which is costly in terms of the labor and machinery expenses incurred in multiple applications.

An example would be the use of a bioactive material having a specific gravity greater than one, used for the treatment of aquatic organisms that persisted at the surface of a body of water.

Similar problems would also occur where the bioactive material has a specific gravity less than one, and the aquatic organisms have a habitat beneath the surface of, or at the bottom of a body of water. In this case, the bioactive material could be injected by means of a tube or other device beneath the surface of the water, but since it has a specific gravity less than one, it would not persist in the region where it is delivered, and would also require multiple applications in order to be effective.

In order to overcome these difficulties, compositions and processes have been provided for treating a column of water where compositions can be specifically formulated to persist either at the top or the bottom of the column or at any planar or volumetric segment in between the top and the bottom.

One composition of matter of the present invention is based on at least one bioactive agent for treating a population of one or more aquatic organisms, at least one carrier component, and at least one coating component for regulating the controlled release rate, and release profile of the bioactive agent in water, with or without one or more binder components for agglomerating said composition into larger units such as granules, pellets, and briquets, or additional formulation ingredients.

A second composition of matter is based on at least one bioactive agent for treating a population of one or more aquatic organisms, at least one joint-function carrier component that is also a coating component for regulating the controlled release rate, and release profile of the bioactive agent in water, with or without one or more binder components for agglomerating said composition into larger units such as granules, pellets, and briquets, or additional formulation ingredients.

A third composition of matter is based on at least one bioactive agent for treating a population of one or more aquatic organisms, at least one joint-function carrier component that is also a coating component for regulating the controlled release rate, and release profile in water, and at least one additional component such as an additional coating component to further regulate or modify the controlled release rate, and release profile of the bioactive agent in water, with or without one or more binder components for agglomerating said composition into larger units such as granules, pellets, and briquets, or additional formulation ingredients.

The various components are selected to sink or float so that each complex or composition will permeate, and remain in any planar or volumetric segment of a water column for a period of time sufficient to effectively treat a population of one or more aquatic organisms.

The aforementioned compositions of matter of the present invention can be placed in one or more differentially water soluble, flexible or rigid, degradable or biodegradable packets, pouches, capsules, canisters, extrusions, coatings, and the like, of polyvinyl alcohol, polyethylene oxide, and hydroxypropyl methyl cellulose films of various thicknesses (e.g., 1–3 mil) to further modify the coating regulated controlled release rate, and release profile of the bioactive agent(s) formulated in the powdered or agglomerated compositions.

Furthermore, the controlled release rate, and release profile of one or more bioactive agents from all compositions of matter of the present invention can be optionally modified by placing said compositions (i.e., powdered or agglomerated) into various shaped (e.g., spherical, cylindrical, etc.) disposable or reusable, biodegradable, degradable or nondegradable, dispensers (e.g., plastic or metal) such as water soluble polyvinyl alcohol pouch 10 having a continuous outer wall 12 that envelops the composition of the invention therein (not illustrated) or metal container 14 having outer wall 16 and bottom wall 18 and 20, with one or more orifices (e.g., holes, slots, etc.) 22 and 24 through which the bioactive agent formulation therein (not illustrated) will be delivered.

Dispensing devices can be of various densities for use in aqueous environments, and can be anchored in various surface, and/or subsurface locations of an aquatic habitat or can be freely dispensed to float, and/or sink at will. These optional dispensing devices can also be utilized in pretreatment or dry aquatic habitats that are scheduled to become aquatic e.g. by the advent of rain, and/or tides.

The carrier comprises a material that will float or sink, and is based on either inorganic or organic compounds that are hydrophobic or hydrophilic. Materials that are especially of interest in this regard are silicas (including sand and diatomaceous earth), cellulose fibers such as PRE-CO-FLOC® which is derived from purified virgin wood pulp, which is fully bleached in a sulfite pulp process having an average fiber length of from about 50 to about 90 microns, and a thickness of from about 7 to 30 microns, metal oxides, clays, infusorial earth, slag, or lava, all of which are finely ground or have a small particle size, but can be agglomerated into larger components with the addition of a binder component. Hydrophilic materials that have been surface treated to be hydrophobic, e.g., by a silicone coating are also suitable. Other carriers include films of polyvinyl alcohol, polyethylene oxide, and hydroxypropyl methyl cellulose, MONO-SOL® LXP-1832 which is a FDA approved hydroxypropyl methyl cellulose (MHPC) and is edible, MONO-SOL® PXPN-1257 MHPC, and the MONO-SOL® 6000, 7000 and 8000 series which are polyvinyl alcohol polymer or copolymer films, thermolytically processed hydrophobic "pin chips" (waste wood, or saw dust) (Sea Sweep®), cetyl alcohol, stearyl alcohol, vermiculite, ground cork, corn cob grits, bagasse from sugar cane or grapes and the like, seed hulls such as rice hulls, or any cereal crop hulls such as oat hulls, wheat hulls barley hulls and the like, paper, and especially dust free paper granules such as BIODAC®, manufactured from recycled, cellulosic based paper waste and containing from about 47 to about 53 wt. % paper fiber, from about 28 to about 34 wt. % clay, and especially paper grade clays or mixtures thereof, including Kaolin, about 14 to about 20 wt. % calcium carbonate or art known equivalents thereof and mixtures thereof, and from about 0.01 to about 0.9 wt. % of an inorganic pigment such as titanium dioxide, or the art known equivalents thereof, and mixtures thereof. Other materials that may be employed as carriers include particulate, i.e. granular or powdered carbon materials including powdered or granular charcoal, peteroleum coke, coke from coal, CVD carbon, carbon black, lamp black, activated carbon, and graphite, powdered polymeric materials, such as powdered olefinic polymer materials, e.g., homopolymers, and/or copolymers of polyethylene or polypropylene, fluorinated polymers such as polytetrafluoroethylene, or polyvinylidene fluoride, or chlorinated polymers such as polyvinylchloride homopolymers and copolymers, acrylate polymers such as acrylic acid and alkyl acrylic acids or esters or amides including the homopolymers and copolymers thereof, and the like. Polysaccharides can also be employed as carriers including starches and modified starches, especially as both are described herein, carrageenen, algin, which is intended to include alginates as well, xanthates, and agar. The carriers can be combined to alter or enhance the performance characteristics of a composition, two, three or four carriers being especially suitable in this regard.

The especially preferred materials in this regard comprise silicas and silicates.

Precipitated silicas employed in this regard are produced from solutions of water glass into which sulfuric acid is introduced under fixed conditions. They are formed in the aqueous phase, and depending on the conditions of precipitation, it is possible to produce products with smaller or somewhat larger primary particles, which then basically determine particle size and specific surface area. The precipitates obtained are then washed and dried by methods known in the art.

Silicates are also manufactured by a precipitation method, however, the acids which are necessary for precipitation are replaced partially or completely by solutions of metallic salts such as aluminum sulfate, and the like. The precipitation parameters can also be adjusted to suit the various raw materials.

The silicas obtained in this way can be dried by a spray drying technique to obtain particles that are substantially spherical, have a size anywhere from about 50 to about 150 $\mu$m, and have excellent flow properties.

Spray dried precipitated silicas may also be ground so that the densities will vary anywhere from about 80 g/l to about 270 g/l, and the particle size anywhere from about 4 $\mu$m to 100 $\mu$m.

Precipitated silicas and silicates can also be dried by standard drying processes, for example in turbo-driers or rotating driers. Silicas and silicates dried in this conventional way must always be subsequently ground. The average particle size and the tapped density also depend on the degree of grinding. The tapped density in this regard can be from about 80 g/l to about 240 g/l, and the particle size from about 4 $\mu$m to about 15 $\mu$m.

Silicas can also be produced by means of a high temperature flame hydrolysis during which silicon tetrachloride is hydrolyzed in an oxyhydrogen flame, which is sometimes referred to as pyrogenic silica. The tapped density of these silicas is somewhere around 50 g/l. Both the precipitated silicas and the pyrogenic silicas can be after-treated in a secondary stage in order to change the naturally hydrophilic surface to a hydrophobic surface e.g. by a suitable chlorosilane to react with a silanol group on the surface of the silica.

The silicas and silicates are further described in *Technical Bulletin Pigments, Synthetic Silicas For Plant Protection and Pest Control*, No. 1 Degussa, Pig. 27-6-2-79OME, 5th Ed., Date of Issue: Jul. 19, 1990, CAB-0-SIL® FUMED SILICAS, TD-117 7M/11/92, Copyright 1990 Cabott Corporation, and Bergna, *The Colloid Chemistry of Silica*, ACS, 1994 all of which are incorporated herein by reference.

Silicas that are especially suitable, include both the hydrophilic and the hydrophobic silicas which have been treated with a chlorosilane, and generally have a surface area of from about 50 to 450 m$^2$/g, an average agglomerate size of from about 3.5 to about 100 $\mu$m, or an average primary particle size of from about 12 to 30 nm, a tapped density of from about 50 to 240 g/l, a pH of from about 3.6 to about 9, and a DBP adsorption of about 160 to 335 g/100 g.

The silicates that may be employed in this regard comprise those that have a surface area from about 30 to about 40 m$^2$/g, an average agglomerate size of from about 4 to about 6 $\mu$m, a tapped density of from about 285 to 315 g/l, a pH of from about 9.5 to about 10.5, and a DBP adsorption of from about 150 to about 170 g/100 g.

The other inorganic carriers and some of the polymeric organic carriers noted in this regard will also have substantially the same surface area and particle size, although the density will vary depending upon the material employed. Larger surface areas and particle sizes can also be utilized. Extruded films that are water-soluble can also be effective carriers in certain formulations. Other carriers that may be employed are described by Stilman, *Immobilization On Polymers*, 1983 which is incorporated herein by reference.

The various bioactive agents that are employed in the compositions of the present invention to treat populations of adult or immature (e.g., egg, larvae, pupae, nymphs) organisms comprise technical or formulated (technical plus inerts) pesticides, insecticides, toxicants, monomolecular surface films, petroleum oils, insect growth regulators, plant growth regulators, animal growth regulators, microbial control agents, pharmaceuticals, medicaments, antibiotics, pathogens, bioactive control agents, parasites, pharmaceuticals or medicaments, bactericides, and viricides, fungicides, algaecides, herbicides, nematicides, amoebicides, acaricides, miticides, predicides, schistisomicides, molluscicides, larvicides, pupicides, ovicides, adulticides, nymphicides, attractants, repellents, growth stimulants, feeding stimulants, nutrients, hormones, chemosterilants, or pheromones, and combinations thereof, such as the two, three or four component combinations. Two or more bioactive agents can be combined in the same composition to achieve multifunctional performance from a single application.

Insecticidal bioactive materials include *Bacillus thuringiensis*, and especially subspecies *kurstaki* and *israelensis, Bacillus sphaericus, Bacillus popilliae, Seriatia marcescens,* and *Lagenidium giganteum*, which are sometimes referred to as bioactive agents employed for the control of insects. Fungal larvicides may also be employed such as *Lagenidium giganteum mycelium* or *Lagenidium giganteum oospores* or mixtures thereof. Pyrethrin and pyrethroid larvicides can also be used. Fungal materials can also be effective against mosquito larvae. Insect growth regulators can be used such as (S)-methoprene, diflubenzuron, or pyriproxyfen. Aliphatic petroleum hydrocarbons may also be used as mosquito larvicides or non-petroleum hydrocarbon oils that form a monomolecular film on the water to be treated. Compositions and processes for control of various species of mosquitoes, and other pest dipterans in aquatic habitats are of particular interest. Bioactive agents of specific interest for use in these compositions include *Bacillus thuringiensis var. israelensis, Bacillus sphaericus, Lagenidium giganteum,* methoprene, diflubenzuron, pyriproxyfen, temephos, 2 mol ethoxylate of isostearyl alcohol, lecithins, and petroleum oils, and combinations thereof, such as the two, three or four component combinations. Other insecticides may also be employed including products such as malathion, resmethrin, dichlorvos, bendiocarb, fenitrothion or chlorpyrifos. Insecticides such as pyrethrin and pyrethroid can be effective as larvicides for mosquitoes.

Various herbicides that may be employed, especially effective aquatic herbicides include Amitrole®, ammonium sulfamate, Bromacil®, copper salts, dalapon, Dichlorbenil®, Diquat®, Diuron®, Endothall®, Fenac®, Picloram®, Prometon®, Silvex®, Simazine®, trichloroacetic acid, 2,4-D, 2,4,5-T, Velpar®, TSMA, dicamba, endothall, silvex, prometon, chlorate, sodium metaborate, monuron, and various combinations thereof, such as the two, three or four component combinations. Other insecticides, herbicides or fungicides that may be employed are set forth by Page & Thomson *The Quick Guide,* Thomson publications 1987, Thomson, *Agricultural Chemicals,* Book I, Insecticides; Book II, Herbicides; Book III, Fumigants, Growth Regulators, Repellants, 1985–87 revisions, all of which are incorporated herein by reference.

Control of floating and submersed aquatic weeds is also of special interest. Bioactive agents included in the compositions and processes for these applications include acrolein, aromatic solvents (xylene), copper sulfate and other water soluble copper salts or compounds, dalapon, dichlorbenil, 2,4-D, diquat, endothall, glyphosate, simazine, and fluridone, and combinations thereof, such as the two, three or four component combinations.

The aquatic organisms that are of special interest and which can be treated by the compositions of the present invention, and in accord with the methods of the present invention include disease carrying or biting or non-biting insects (e.g., mosquitoes, sand flies, black flies, midges), or other animals (e.g., fish, barnacles, snails) or aquatic and wetland plants, and especially parasitic animals (e.g., nematodes, mollusks, protozoans, and bacteria) or floating or submersed nuisance weeds e.g., algae, duckweed, hydrilla, water hyacinth, chara, watermilfoil, cattail bass weed, burreed, coontail, and the various pondweeds including bushy, curly-leaf, flat stem, floating-leaf, horned, and sago; water star grass, arrowhead, bladderwort, bulrush, hornwort, creeping water primrose, pickerelweed, spatterdock, cow lily, yellow water lily, waterweed, water chestnut, water smart weed, white water lily, naiad, watershield, elodea, hydrollia, alligatorweed, cattails, giant cutgrass, guineagrass, knotgrass, maidencane, paragrass, phragmites, spatterdock, and torpedograss.

It should be noted that any bioactive agent, and combinations thereof, such as the two, three or four component combinations, designed for promoting (e.g., nutrients) or terminating (e.g., pesticides, or herbicides) the life of aquatic or terrestrial organisms can be utilized in the compositions of matter, depending on the desired end result. Specific controlled release compositions will be designed to deliver the desired bioactive agent(s) in the targeted portion(s) of the water column of an aquatic habitat.

These bioactive materials, and organisms are further described by Levy in U.S. Pat. Nos. 4,818,534, columns 12–14; 4,983,389, columns 11–13; 4,985,251, columns 4, 10, and 12–14; all the foregoing being incorporated herein by reference.

The coatings that may be employed according to the present invention are selected so as to act as materials that will regulate the controlled release rate and release profile of bioactive agents over a period of time in an aqueous medium, and accordingly have to be water soluble or partially water soluble and biodegradable, or insoluble in water, and biodegradable or erodible, and/or film-forming on contact with water. Coatings may also protect bioactive agents from photodegradation or biodegradation. The coatings have a specific gravity equal to or greater than one or less than one, and are liquids or solids, and generally consists of either fatty alcohols or acids, or fatty alcohol esters of citric, glycolic, trimelletic or phthalic acid, or any mono, di- or tricarboxylic acid having from one to about 18carbon atoms, whether saturated or unsaturated, aliphatic or cyclic, and which are well known in the art. The fatty alcohols in this regard comprise those alcohols having from about 5 to about 18 carbon atoms, and include the saturated as well as unsaturated aliphatic fatty alcohols. The aliphatic acids or -alcohols include the straight chain and branched chain isomers.

The coatings having a specific gravity less than one may comprise n-butyryl-tri-n-hexyl citrate, monostearyl citrate, stearyl alcohol, cetyl alcohol, myristyl alcohol, octadecanoic acid, glyceryl stearate, or waxes whereas the coatings having a specific gravity greater than one comprise, triethyl citrate, acetyltriethyl citrate, tri-n-butyl citrate, acetyltri-n-butyl citrate, acetyltri-n-hexyl citrate, tri-n-hexyltrimellitate, dicyclohexyl phthalate, diethyl phthalate, butyl phthalyl butyl glycolate, dimethyl isophthalate, or water-soluble films of polyvinyl alcohol, polyethylene oxide, methyl cellulose, paper, and hydroxypropyl methyl cellulose, and combinations thereof, such as the two, three or four component combinations. It should be noted that water-soluble films can act in a coating/carrier capacity in certain compositions of matter. Two or more coatings can be combined to modify or enhance the controlled release rate or release profile of one or more bioactive agents in a composition.

The coatings, bioactive agents and carriers may also be combined with water soluble or insoluble, hydrophilic or hydrophobic, biodegradable or erodible, cross-linked or non-crossed-linked, binder materials such as sulfonated polystyrene homopolymers, sulfonated styrene maleic anhydride polymers, sulfonated vinyl toluene maleic anhydride polymers, vinyl pyrrolidone polymers or copolymers, poly (isobutylene-co-disodium maleate) copolymers, acrylamide polymers or copolymers, acrylonitrile-starch graft polymers or copolymers, carboxymethyl cellulose polymers or copolymers, acrylate polymers or copolymers, poly(vinyl alcohol) polymers or copolymers, poly(ethylene oxide) polymers or copolymers, acrylic acid or acrylic ester homopolymers or copolymers, modified food starch (CAPSUL® and N-LOCK®), natural or synthetic gums, poly(ethylene glycol), clays, gypsum, plaster of paris, wax, paper, and especially paer as described herein including without limitaion, BIODAC®, cellulose, latex, methyl vinyl ether maleic acid ester copolymers, and various starches and modified starches as described by Davidson *Book Of Water-Soluble Gums And Resins,* 1980, chapter 22, BP.22-1 to 22–79 which is incorporated herein by reference, and combinations thereof such as the two, three or four component combinations to agglomerate the controlled release compositions into larger units such as granules, pellets, briquets, or extrusions.

The foregoing polymers or copolymers which comprise superabsorbent polymers are especially useful in forming agglomerates of the compositions of the present invention. The various processes are known for forming these agglomerates some of which are described in *Ferro-Tech General Catalog,* Form 317, 8-1-83, revised 12–85 which is incorporated herein by reference, and is published by the Ferro-Tech® Corporation, 467 Eureka Road, Wyandotte, Mich. 48192, which is incorporated herein by reference.

The controlled release compositions may also be combined with other formulating materials or ingredients or components wherein such components are diluents, adjuvants, dyes, alcohols, acetone, ketones, oils, surfactants, water, emulsifiers, film-forming agents, compatibility agents, wetting agents, salt, natural or synthetic polymers, hydrocolloids, buoyancy modifiers, ultraviolet absorbers, photo-protecting agents, suspending agents, elastomers, penetrants, deflocculating agents, dispersing agents, stabilizing agents, antifoaming agents, sticking agents, solvents, co-solvents, catalysts, or synergists, and the like, and combinations thereof, such as the two, three or four component combinations.

Components of the present invention can be homogeneously or hetrogeneously combined into the desired controlled delivery compositions or complexes for treating a population of aquatic organisms in an aquatic or preaquatic environment by admixing the individual solid, and/or liquid formulation components in a concentration, and order to effectively impregnate or encapsulate the carrier(s) with the desired concentration of coating agent(s) and bioactive agent(s).

Admixing with one or more optional binders, and/or formulation materials can be utilized to agglomerate the composition(s) into larger units, and/or to achieve optimum controlled release performance. Formulation components can also be fabricated into solid controlled delivery compositions by coupling aqueous admixing procedures with solvent based admixing procedures.

To further modify the controlled delivery rate and release profile of compositions of matter of the present invention, powdered or agglomerated compositions can be placed into flexible or rigid polyvinyl alcohols, polyethylene oxide, and/or hydroxypropyl methyl cellulose film containers (e.g., pouches, packets, capsules, extrusions) of varying water solubilities. In addition, compositions can be optionally placed into various shaped (e.g., spherical, cylindrical, etc.) dispensers (e.g., plastic, glass, metal, etc.) having a specific gravity greater than or less than one, with one or more orifices (e.g., holes, slots, etc.) in the wall(s) of the dispensing device to modify the controlled release rate and release profile of the bioactive agent from the compositions of matter through the orifice(s) into a water column. Pretreatment application of these dispensing devices is also within the scope of the present invention.

An example of a commercially available products that may be employed in this regard comprise DISSOLVO™-POUCH which is a polyvinyl alcohol film pouch. The various dimensionally stable solvable pouches are further describe by Miller in *Pesticides Formulations and Application System;* 8th Vol., ASTM STP 980, D. A. Hovde et al., EDS. American Society for Testing and Materials, Phil. 1988, which is incorporated herein by reference.

The compositions of the present invention can be formulated to time-release one or more bioactive agents from the carrier to treat a population of organisms in specific areas of a water column of an aquatic environment according to zero-order, first-order, or square-root-of-time kinetics. In general, depending on the type, concentration, and number of coatings utilized on a composition, and the formulation procedures utilized in fabricating the compositions, controlled delivery of one or more bioactive agents from the carrier can be fast, slow, delayed or pulsed. Controlled release formulations can be prepared wherein the materials for the preparation of such controlled release compositions are described by Wilkins, *Controlled Delivery Of Crop-Protection Agents,* 1990, Kydonieus, *Controlled Release Technologies: Methods, Theory And Applications,* Volumes 1 and 2, 1980; Barker *Controlled Release Of Biologically Active Agents,* 1987, Marrion, *The Chemistry And Physics Of Coatings,* 1994; Muller *Carriers For Controlled Drug Delivery And Targeting,* CRC press; Duncan and Seymour, *Controlled Release Technology* 1989; and Karsa and Stephenson, *Encapsulation And Controlled Release* 1993, all of which are incorporated herein by reference.

Controlled release solid compositions utilized in the present invention for treating a population of one or more aquatic organisms consist of about 0.001% to about 50% by weight (w/w) of at least one coating agent, about 0.0001% to about 50% (w/w) of at least one bioactive agent, and about 50% to about 99% (w/w) of at least one carrier; with or without about 0.0001% to about 75% (w/w) of one or more binders, and/or one or more formulating materials or about 0.1% to about 99.9% (w/w) of at least one joint-function carrier/coating agent, about 0.001% to about 90% (w/w) of at least one bioactive agent; with or without about 0.0001% to about 75% (w/w) of one or more binders, and/or one or more formulating materials.

Controlled release solid compositions utilized in the present invention for specifically treating a population of one or more species of mosquitoes in their aquatic stages, typically consist of about 1.0% to about 25% (w/w) of at least one coating agent, about 0.01% to about 30% (w/w) of at least one bioactive agent, and about 70% to about 95% (w/w) of at least one carrier; with or without about 0.01% to about 60% (w/w) of one or more binders, and/or formulating materials or about 50% to about 99% (w/w) of at least one joint-function carrier/coating, about 0.1% to about 30% (w/w) of at least one bioactive agent; with or without about 0.01% to about 60% (w/w) of one or more binders, and/or formulating materials. Solid compositions of the present invention can optionally be suspended in water or oil for application as a liquid spray.

In the embodiment of the present invention comprising complexes for treating a population of one or more aquatic organisms in a column of water, the complexes comprise at least one controlled delivery system, and especially from__ about one to about three controlled delivery systems. Each controlled delivery system in turn comprises at least one carrier, at least one bioactive agent as a component for treating a population of one or more aquatic organisms, and at least one coating component or at least one joint-function carrier/coating agent for regulating the controlled release rate and release profile of the bioactive agent in water with or without one or more binder components as an agglomeration aid or one or more additional formulation materials, which is intended to mean anywhere from one to about three of each of these components.

By properly selecting one or more of the various bioactive components, and/or other components, a composition of matter can be provided that will be effective to treat a population of one or more aquatic organisms or a plurality of aquatic organisms at either the surface, subsurface, the bottom or, the entire column of water.

Each one of these components is selected to sink or float so that the complex will permeate and remain in any planar or volumetric segment of a water column for a period of time sufficient to treat a population of one or more aquatic organisms.

It should be noted in this regard that even though silica has a specific gravity greater than one, a finely divided silica that has been surface treated with silicone, as noted herein, will float because of the hydrophobic properties imparted to it by the silicone coating. Accordingly, the hydrophobicity of the components in the composition of matter has to be taken into account when formulating the composition of the present invention by adjusting the type, and/or quantity of the hydrophobic component(s) employed.

Similarly, the density or the flotation properties of the other components of the compositions of matter of the invention have to be taken into account, as well as the quantity of such components when formulating the compositions of the invention so that it will be delivered to the appropriate planar or volumetric segment of the column of water that is to be treated according to the processes of the invention. When this formulation method is employed, a controlled delivery composition of matter can be prepared having a buoyancy selected to treat any part of a water column, or an entire water column.

Thus, a controlled delivery composition of matter can be prepared based on a carrier that sinks, and a bioactive material and coating that floats, each being employed in amounts that can be readily determined, so that the bioactive material will be taken to the bottom of a water column by the carrier, and upon exposure to water in the column, the coating will be released, and carry the bioactive material to the surface to treat any surface organisms or any organisms encountered in moving toward the, surface. An example of a controlled delivery system like this comprises sand coated with the optimum concentration of cetyl alcohol in combination with a bioactive material that floats.

Similarly, a carrier can be selected that floats in combination with a coating that floats, and a bioactive material that sinks, where the types and quantities of each are experimentally determined so that the composition floats. Upon exposure to water, the coating will release the bioactive material which will move towards the bottom of the column, and treat any aquatic organisms that are at the bottom or encountered in moving toward the bottom of the column. An example of a controlled delivery composition of matter that will function in this way comprises silica that floats, i.e., hydrophobic finely divided silica coated with a silicone material, in combination with cetyl alcohol, and any known bioactive material that sinks.

Another controlled delivery composition of matter can be prepared based on a carrier and bioactive agent that sinks, and a coating that floats each being employed in amounts that can readily be determined so that the bioactive material will be taken to the bottom of a water column by the carrier, and upon exposure to the water the coating will be released, and initially carry the bioactive agent to the surface to treat any surface organisms encountered in moving toward the surface, and then after being maintained at the surface for some period of time, the bioactive agent will slowly move toward the bottom where it will be available to treat organisms on the downward movement through the water column, and at the bottom of the water column. An example of a controlled delivery system like this comprises sand coated with an optimum concentration of cetyl alcohol in combination with a bioactive agent that sinks.

Furthermore, compositions of matter of the invention comprising a joint-function carrier/coating agent, and bioactive agent, such as a sinking, and/or floating joint-function carrier/coating agent, or a joint-function carrier/coating agent, an additional coating agent, and a bioactive agent can be developed to distribute a bioactive agent to desired areas or volumes of a water column over time, or to one or more terrestrial organisms over time. Especially suitable joint-function carrier/coating agents comprise polyvinyl alcohol, polyethylene oxide, hydroxypropyl methyl cellulose, cetyl alcohol or stearyl alcohol and various combinations thereof such as the two, three or four component combinations.

All compositions can be optionally combined with a binder to agglomerate the composition into larger units such as granules, pellets, and briquets, or an additional formulation ingredient. In addition, all compositions can also be optionally dispensed in a water column enclosed within water soluble film containers, and/or dispensed from devices having one or more orifices open.

From these descriptions, it is obvious that one or more floating, and/or sinking carriers, coatings, and bioactive agents with or without binders or additional formulation ingredients can be combined in various permutations, and combinations into controlled release compositions that are designated to target desired areas or volume segments of a water column or an entire water column to treat a population of one or more aquatic organisms.

It should be noted in this regard that the water column is defined as a volume of water underneath the surface of water of a specified area that requires treatment, the body of water including ponds, lakes, bays, wetlands, marshes, swamps, tidal basins, lagoons, sounds, creeks, streams, rivers, oceans, ditches, swales, sewage treatment controlled delivery systems, potholes, tree holes, rock holes, bromeliads, tires, which is to say moving or stagnant water containing one or more target organisms. Thus, the treated column of water can be either moving or stationary, and have any water quality that can be utilized as a habitat for the target organism(s).

By treating a column of water, as that term is employed herein, it is intended not only to provide the compositions of matter of the present invention to a column of water that is infested with aquatic organisms that exist in the column, but also a column of water that has the potential of being infested with aquatic organisms. Compositions of matter of the present invention are also provided for pretreatment application to a dry habitat that has not yet flooded by rain, tides, and the like, to produce a defined water column where aquatic organisms are known to breed, i.e. a preflood area. Compositions of matter for pretreatment of an existing water column that is not yet infested with aquatic organisms or that are infested with organisms are also within the scope of the invention.

The compositions of the present invention can be applied by ground or aerial techniques as dry powders, agglomerates such as granules, pellets, and briquets, and encapsulated within water soluble or degradable pouches or capsules of polyvinyl alcohol, polyethylene oxide, hydroxypropyl methyl cellulose, paper, or gelatin, and/or within devices having one or more orifices in contact with the water column. The compositions of the present invention can also be applied as water, and/or oil based formulations.

In the following examples powdered and agglomerated controlled delivery compositions of matter are utilized as examples to illustrate the present invention, and were designed to target surface, subsurface, or both surface, and subsurface areas of an aquatic habitat. Larvae of *Anopheles* spp. mosquitoes were used as models to demonstrate the efficacy of surface active compositions, while larvae of *Aedes* spp. and *Culex* spp. mosquitoes were used to demonstrate subsurface efficacy.

Insecticidal bioactive agents admixed with a variety of carriers and coatings or joint-function carrier/coatings, with or without binders or formulating materials, were commercial formulations of the bacteria *Bacillus thuringiensis var. israelensis* (B.t.i.) (Acrobe® Technical Powder, Acrobe® Biolarvicide or Vectobac® Technical Powder), the insect growth regulator methoprene (Dianex® Emulisifiable Concentrate), a mixture of Acrobe® TP, and Dianex® EC, the organophosphate temephos (Abate® 4-E) or an experimental monomolecular surface film (POE(2) 2 mol ethoxylate of isostearyl Alcohol). Additional insecticidal bioactive agents admixed with a variety of coatings and carriers, with or without binders or formulation materials, that were not utilized in mosquito bioassays, were commercial formulations of the insect growth regulators diflubenzuron (Dimilin® Wettable Powder) or pyriproxyfen (Nylar® Technical or Emulsifiable Concentrate), the bacteria *Bacillus sphaericus* (ABG-6184), the fungus *Lagenidium giganteum*, and the petroleum oil (GB-1111). Examples of liquid or solid coatings utilized in the compositions of matter to regulate the controlled release rate and release profile of the bioactive agent(s) from the carrier were esters of citrate (Citroflex®2, A-2, 4, A-4, A-6 or B-6), phthalate, glycolate, trimellitate (Morflex® 150, 190, or 560), cetyl alcohol, and/or polyvinyl alcohol films (MonoSol® 7000 or 8000 series). Coatings ranged from water soluble to insoluble, and had specific gravities less than or greater than one. Solid carriers utilized in the compositions of matter as surface or subsurface-active bioactive agent delivery matrices were hydrophobic (Sipernat®D17, and Aerosil®R972) or hydrophilic (Wesslon™, Wesslon™ 50, Sipernat®22S, and FK 500 LS) Degussa silicas, sand (Texblast®), cetyl alcohol (Sigma®) (specific gravity less than one), and/or polyvinyl alcohol films (MonoSol®7000 or 8000 series ) (specific gravity greater than one). Polymeric binders utilized in the examples to agglomerate the powdered compositions into larger units were soluble starch (Difco®), sulfonated polystyrene (Versa®TL-502), sulfonated vinylic copolymers (Narlex® D-82), acrylic copolymer (Carboset®514H), and acrylic polymer (Carbopol®ETD 2001 Resin). Additional formulation materials such as water, soluble or insoluble alcohols (2-propanol, 2-ethyl hexanol, 2 mol ethoxylate of isostearyl alcohol) or ketones (acetone, methyl ethyl ketone) were also utilized as admixture components in selected compositions.

A series of bioassays were designed to demonstrate the short or long-term mosquito- controlling effectiveness of a variety of powdered and agglomerated compositions that were formulated to time-release one or more mosquitocidal bioactive agents in specific areas of a water column or the entire water column. Composition transfer bioassays were utilized to evaluate the controlled release duration of selected powdered or agglomerated formulations. The efficacy of pretreatment compositions was also evaluated. Powdered or agglomerated compositions were evaluated at ca. 27° C. in 0.019 m$^2$ ½ gal plastic containers containing 1000 ml of fresh water (purified by reverse osmosis filtration) or brackish (10% Instant Ocean®/distilled water) water and ten 1st to 4th instar larvae of the *Anopheles, Aedes,* or *Culex* species. Bioassays were also conducted with mixed species populations. Tests with each powdered or agglomerated controlled delivery composition were replicated three times.

The following examples are illustrative of the controlled delivery fabrication protocols, types of powdered and agglomerated controlled release compositions, and processes for treating a population of aquatic organisms in a column of water.

EXAMPLE 1

The admixing protocol for the components utilized in the powdered composition (Code J) in this bioassay series against mosquito larvae was as follows: 10 g cetyl alcohol (heated to 60° C.) and 5 g triethyl citrate (Citroflex®2) were each added separately to 300 g acetone in ½ gal plastic beakers and mixed with a laboratory hand mixer (GE® Model 420A) for ca. 5 minutes. 5 g of B.t.i. (Acrobe®TP) was then slowly added to each coating formulation while mixing for an additional 5 minutes. 85 g and 90 g hydrophobic silica (Sipernat®D17) were slowly added to the cetyl alcohol and triethyl citrate formulations of bacteria, respectively, while mixing for an additional 2½–3 hr to drive off the acetone and assure that the B. t.i. and each coating were uniformly impregnated on the silica carrier. Powdered compositions were placed in a low humidity room (27–38% RH; 76–79° F.) for an additional 4 hr to assure volatilization of the acetone. Each powdered formulation was stored in zip-lock (trade mark) bags or glass bottles. Sub samples of each of the two formulations were admixed at a 1:1 ratio for an additional 5 minutes to achieve the powdered composition utilized for testing.

Results of short-term bioassays against *Anopheles, Aedes,* and *Culex* species in fresh or brackish water with a powdered controlled delivery composition comprising a 1:1 blend of an acetone-base (300 g) admixture formulation (w/w) of 5 g of B.t.i. (specific gravity greater than one/ insoluble in water) labeled Acrobe®TP (3864 ITU/mg), 10 g cetyl alcohol (specific gravity less than one/insoluble in water), and 85 g hydrophobic silica (Sipernat®D17) and another acetone-base (300 g) admixture formulation (w/w) of 5 g Acrobe®TP, 5 g triethyl citrate (Citroflex®2; specific gravity greater than one/water soluble), and 90 g Sipernat®D17 indicated that the multiply coated/ encapsulated B.t.i. could be released from the hydrophobic silica carrier at varying intervals/rates and provide effective control of both surface and subsurface feeding mosquito larvae at extrapolated application rates of ca. 2.5 lb/surface acre of water (Table 1). The efficacy of the composition against the *Anopheles* species indicated that Acrobe®TP can be maintained at the surface feeding area of an aquatic habitat for a sufficient period of time to effectively allow the *Anopheles* larvae to ingest lethal concentrations of toxic crystals of B.t.i. Efficacy against *Aedes* and *Culex* species suggested that the dense B.t.i. was slowly released from the surface-active carrier/coating formulation below the surface of the water through the water column where the toxic crystals were accessible to the subsurface and bottom feeding species. In general, the powdered controlled delivery composition was effective in releasing sufficient concentrations of B.t.i. over a 1 to 5 day posttreatment period to produce 100% control of surface or subsurface feeding mosquito larvae in fresh or brackish water. Controlled release of B.t.i. from the silica carrier to surface and/or subsurface areas of a water column was a function of the type and concentration of coating agents. The initial point of B.t.i. release and distribution at the water interface was a function of the hydrophobic nature of the carrier.

TABLE 1

Example 1. Coating-Regulated Delivery of Acrobe ® TP from a Hydrophobic Silica Carrier*

| Mosquito Species | Larval Instar | Water Quality | % Control of Larvae at Indicated Posttreatment Time Period(Days)** | | | | |
|---|---|---|---|---|---|---|---|
| | | | 1 | 2 | 3 | 4 | 5 |
| Surface Feeder (*Anopheles spp.*) | | | | | | | |
| *An. albimanus* | 2nd | Fresh | 100.0 | — | — | — | — |
| *An. albimanus* | 3rd | Fresh | 83.3 | 90.0 | 100.0 | — | — |
| *An. albimanus* | 4th | Fresh | 23.3 | 60.0 | 80.0 | 100.0 | — |
| *An. albimanus* | 2nd | Brackish | 90.0 | 100.0 | — | — | — |
| *An. albimanus* | 3rd | Brackish | 83.3 | 96.7 | 100.0 | — | — |
| *An. albimanus* | 4th | Brackish | 53.3 | 76.7 | 96.7 | 100.0 | — |
| *An. quadrimaculatus* | 2nd | Fresh | 100.0 | — | — | — | — |
| *An. quadrimaculatus* | 3rd | Fresh | 70.0 | 100.0 | — | — | |
| *An. quadrimaculatus* | 4th | Fresh | 50.0 | 50.0 | 53.3 | 96.7 | 100.0 |
| Subsurface Feeder (*Aedes* and *Culex spp.*) | | | | | | | |
| *Ae. aegypti* | 1st | Fresh | 100.0 | — | — | — | — |
| *Ae. aegypti* | 3rd | Fresh | 53.3 | 90.0 | 100.0 | — | — |
| *Ae. taeriorhynchus* | 3rd | Brackish | 90.0 | 93.3 | 96.7 | 100.0 | — |
| *Cx. quinquefasciatus* | 3rd | Fresh | 26.7 | 43.3 | 83.3 | 100.0 | — |

5% Acrobe ®TP (w/w) utilized in the controlled release composition. Cetyl alcohol and triethyl citrate utilized as B.t.i. release-rate regulators (formulation ratio of 1 part cetyl alcohol/B.t.i. to 1 part triethyl citrate/B.t.i.).
** B.t.i. compositions applied as a powder at ca. 2.5 lb/acre.

EXAMPLE 2

Another series of bioassays with other types of powdered controlled release compositions were conducted against larvae of *Anopheles, Aedes,* and mixed populations of *Anopheles* and *Culex* species in fresh and brackish water. In formulating these compositions of matter, B.t.i. (Acrobe®TP) was admixed with other types of hydrophobic (Aerosil®R972) and/or hydrophilic (FK 500 LS) silica, hydrophobic wood "pin chips" or saw dust (Sea Sweep®), or sand (Texblast®) carriers and cetyl alcohol and/or triethyl citrate (Citroflex® 2) coating agents into powdered controlled delivery compositions that had an affinity for targeting selected areas of an aquatic habitat (Table 2).

Results of a series of short-term bioassays with these powdered controlled release compositions are presented in Table 3. The data indicated that the type(s) of powdered carrier(s) (e.g., hydrophobic and/or hydrophilic) and the type(s) and concentration of coating/encapsulation agent(s) e.g., specific gravity greater than and/or less than one/water soluble and/or insoluble) utilized in a powdered composition would dictate the orientation of delivery in a water column and the rate of release of larvicidal bacteria. All powdered compositions provided 100% control of larvae in fresh or brackish water. In general, results indicated that specific carriers and coatings could be combined with B.t.i. in a manner to selectively target subsurface/bottom feeding mosquito larvae or mixed populations of surface and subsurface/bottom feeding mosquito larvae. The type of carrier was observed to initially orient the bioactive agent (i.e., B.t.i.) in a surface or subsurface plane of the water column while the type of coating agents would dictate controlled release persistence, rate, direction, and/or a change in the initially observed surface or subsurface release plane of B.t.i.

TABLE 2

(Example 2). Formulation Components in Powdered Controlled Delivery Compositions*

| Composition No. | Concentration of Admixtures in Powdered Compositions |
|---|---|
| 1 | 5 g B.t.i. (Acrobe ®TP) + 5 g cetyl alcohol + 5 g triethyl citrate (Citroflex ®2) + 42.5 g hydrophobic silica (Aerosil ® R972) + 42.5 g hydrophilic silica (FK 500 LS) |
| 2 | 5 g B.t.i. (Acrobe ®TP) + 10 g cetyl alcohol + 85 g hydrophilic silica (FK 500 LS) |
| 3 | 10 g B.t.i. (Acrobe ®TP) + 10 g triethyl citrate (Citroflex ® 2) + hydrophobic "pin chips" (Sea Sweep ®) |
| 4 | 5 g B.t.i. (Acrobe ®TP) + 20 g cetyl alcohol + 75 g sand (Texblast ®) |

*Cetyl alcohol (heated to 60° C.) and/or triethyl citrate was added to 300 g acetone and mixed for 5 minutes with a GE ® Model 420A hand mixer in a 1/2 gal plastic beaker. B.t.i. was slowly added to solvent-base formulation of coating(s) while mixing for an additional 5 minutes. Hydrophobic and/or hydrophilic silica or sand was admixed with the other components while mixing was continued for ca. 3 hr to drive off the acetone and assure a homogeneous dry mixture of allthe components.
Hydrophobic "pin chips" were ground with a Micro-Mill ® into a fine powder. Triethyl citrate was added to a stainless steel bowl containing 800 g acetone and mixed for ca. 5 minutes with a KitchenAid ® KSM 90 (speed #6) hand mixer. B.t.i. was added slowly and mixing was continued for ca. 5 minutes. Ground "pin chips" were slowly added to the mixture while blending was continued on speed #2 for ca. 4 hr until the powdered formulation was dry.
All powdered compositions were placed in a low-humidity room (ca. 27–38% RH) for ca. 3 hr to assure volatilization of the solvent. Powdered compositions were stored in zip-lock bags or glass bottles.

TABLE 3

Example 2. Coating-Regulated Delivery of Acrobe ® TP From Several Types of
Hydrophobic and Hydrophilic Carriers.*

| Mosquito Species | Larval Instar(s) | Water Quality | Composition No | % Control of Larvae at Indicated Posttreatment Time Period (Days)** | | | | | | |
|---|---|---|---|---|---|---|---|---|---|---|
| | | | | 1 | 2 | 3 | 4 | 5 | 6 | 7 |
| Subsurface Feeders (*Aedes* and *Culex spp.*) | | | | | | | | | | |
| *Ae. aegypti* | 2nd | Fresh | 1 | 76.7 | 90.0 | 96.7 | 100.0 | — | — | — |
| *Ae. aegypti* | 3rd | Fresh | 2 | 93.3 | 96.7 | 100.0 | — | — | — | — |
| *Ae. taeniorhynchus* | 3rd | Brackish | i | 90.0 | 100.0 | — | — | — | — | — |
| *Ae. taeniorhynchus* | 3rd | Brackish | 2 | 63.3 | 90.0 | 100.0 | — | — | — | — |
| *Ae. taeniorhynchus* | 3Td | Brackish | 3 | 40.0 | 83.3 | 96.7 | 96.7 | 100.0 | — | — |
| *Cx. quinquefasciatus* | 3rd | Fresh | 1 | 63.3 | 83.3 | 96.7 | 100.0 | — | — | — |
| *Cx. quinquefasciatus* | 3rd | Fresh | 3 | 93.3 | 100.0 | — | — | — | — | — |
| *Cx. quinquefasciatus* | 4th | Fresh | 1 | 100.0 | — | — | — | — | — | — |
| *Cx. quinquefasciatus* | 4th | Fresh | 2 | 100.0 | — | — | — | — | — | — |
| Subsurface/Surface Feeders (*Culex* and *Mopheles spp.*)*** | | | | | | | | | | |
| *Cx. quinquefasciatus/ An. albimanus* | 3rd/2nd | Fresh | 2 | 83.3 | 93.3 | 93.3 | 96.7 | 100.0 | — | — |
| *Cx. quinquefasciatus/ An. albimanus* | 3rd/2nd | Fresh | 4 | 50.0 | 63.3 | 66.7 | 90.0 | 90.0 | 93.3 | 100.0 |

5% Acrobe ® TP utilized in all controlled release compositions. Cetyl alcohol and/or triethyl citrate utilized as B.t.i. release-rate regulators.
**B.t.i. compositions applied as a powder at ca. 2.5 lb/acre.
***Mixed *Culex* and *Anopheles* larvae (1:1).

EXAMPLE 3

Powdered admixtures of B.t.i. (Acrobe®TP), a hydrophobic silica (Sipernat®D17) carrier, a cetyl alcohol coating, and a soluble starch, sulfonated polystyrene (Versa®TL-502) or sulfonated vinylic (Narlex®D-82) polymeric binder were also agglomerated by hand into a series of controlled delivery briquets (Table 4). Small cubettes (ca. 3.5×3.5×4.5 mm) were sectioned from each type of B.t.i. briquet and utilized in a series short-term bioassays against 2nd instar larvae of *Anopheles* and *Culex* species in fresh and brackish water. One cubette per bioassay test chamber (i.e., plastic ½ gal beakers) was equivalent to an extrapolated application rate of ca. 5 lb/surface acre of water.

Evaluation of 3 types of Acrobe®TP cubettes against *Anopheles* and *Culex* larvae indicated that the rate of control was a function of the coating-regulated release of B.t.i. from the encapsulated silica and the rate of binder-regulated dissociation of the powdered components from the agglomerated matrices in fresh or brackish water (Table 5). Observations indicated that the initial orientation of the Narlex®, soluble starch, and Versa® cubettes on introduction to water was sinks, sinks, and floats, respectively. Dissociation of Narlex® and Versa® cubettes into smaller powder-like components occurred in ca. 5 minutes after introduction into the fresh or brackish water, while soluble starch cubettes dissociated into several small subagglomerated. units in about 24 hr after introduction to fresh or brackish water. The smaller subagglomerated units were observed to dissociate into still smaller powder-like components over a several day period. The hydrophobic silica carrier coated with the insoluble, low specific gravity cetyl alcohol and B.t.i. was observed to float upon being released from the initial surface or subsurface orientation of the cubette in the aquatic habitat. The series of agglomerated B.t.i. compositions produced 100% control of larvae within 1 to 9 days posttreatment.

TABLE 4

(Example 3). Formulation Components in Agglomerated
Controlled Delivery Compositions*

| Composition Code | Concentration of Admixtures in Agglomerated Compositions |
|---|---|
| A | 5 g [5 g B.t.i. (Acrobe. ®TP) + 10 g cetyl alcohol + 85 g hydrophobic silica (Sipernat ®D17)] + 5 g sulfonated polystyrene polymer (Versa ®TL-502) |
| B | 5 g [5 g B.t.i. (Acrobe ®TP) + 10 g cetyl alcohol + 85 g hydrophobic silica (Sipernat ®D17)] + 5 g sulfonated vinylic copolymer (Narlex ®D-82) |
| C | 5 g [5 g B.t.i. (Acrobe ®TP) + 10 g cetyl alcohol + 85 g hydrophobic silica (Sipernat ®D17)] + 5 g soluble starch |

*Cetyl alcohol (heated to 60° C.) was added to 300 g acetone and mixed for ca. 5 minutes with a GE ® Model 420A hand mixer in a 1/2 gal plastic beaker. B.t.i. was slowly added into the solvent-base formulation of coating while mixing for an additional 5 minutes. Hydrophobic silica was mixed with the other components while mixing was continued for ca. 3 hr to drive off the acetone and assure a homogeneous dry mixture of all components. The powdered composition was placed in a low humidity room (ca. 27–38% RH) for ca. 4 hr to assure volatilization of solvent. A ratio of one part of this powdered 3-part bioactive agent/coating/carrier formulation was mixed with one part binder (sulfonated polystyrene polymer, sulfonated vinylic copolymer or soluble starch) for ca. 5 minutes. The 1:1 composition was then hand compacted into 25 × 20 × 5 mm vinyl specimen molds (Cryomold ®) and placed in a high humidity curing room (ca. 80% RH and 80° F.) for ca. 96 hr. Molds containing each composition were then transferred to a drying room (ca. 27–38% RH, 76–79° F.) for an additional 96 hr. The dry solidified briquet compositions in each mold were stored in plastic zip-lock bags. Subsections of each briquet (i.e., ca. 3.5 × 3.5 × 4.5 mm cubettes) were utilized in the bioassays. One cubette (ca. 0.01 g) was utilized against mosquito larvae in each bioassay test chamber (3 replications/agglomerated composition).

TABLE 5

Example 3. Coating-Regulated Delivery of Acrobe ® TP from Agglomerated Compositions*

| Mosquito Species | Water Quality | Composition Code | % Control of 2nd Instar Larvae at Indicated Posttreatment Time Period (Days)** | | | | | | | | |
|---|---|---|---|---|---|---|---|---|---|---|---|
| | | | 1 | 2 | 3 | 4 | 5 | 6 | 7 | 8 | 9 |
| Surface Feeder (*Anopheles spp.*) | | | | | | | | | | | |
| *An. albimanus* | Fresh | A | 93.3 | 100.0 | — | — | — | — | — | — | — |
| *An. albimanus* | Fresh | B | 100.0 | — | — | — | — | — | — | — | — |
| *An. albimanus* | Brackish | A | 90.0 | 100.0 | — | — | — | — | — | — | — |
| *An. albimanus* | Brackish | B | 90.0 | 100.0 | — | — | — | — | — | — | — |
| *An. albimanus* | Brackish | C | 16.7 | 33.3 | 33.3 | 43.3 | 86.7 | 96.7 | 100.0 | — | — |
| *An. quadrimaculatus* | Fresh | A | 93.3 | 100.0 | — | — | — | — | — | — | — |
| *An. quadrimaculatus* | Fresh | B | 96.7 | 100.0 | — | — | — | — | — | — | — |
| Subsurface Feeders (*Culex spp.*) | | | | | | | | | | | |
| *Cx. quinquefasciatus* | Fresh | A | 100.0 | — | — | — | — | — | — | — | — |
| *Cx. quinquefasciatus* | Fresh | B | 93.3 | 100.0 | — | — | — | — | — | — | — |
| *Cx. quinquefasciatus* | Fresh | C | 23.3 | 43.3 | 63.3 | 70.0 | 83.3 | 86.7 | 90.0 | 96.7 | 100.0 |

*5% Acrobe ® TP (w/w) utilized in each agglomerated controlled release B.t.i. composition. Compositions contained B.t.i., a cetyl alcohol coating, a hydrophobic silica carrier, and a sulfonated polystyrene polymer, sulfonated vinylic copolymer, or soluble starch binder (formulation ratio of 1 part bioactive agent/coating/carrier to 1 part binder).
** B.t.i. compositions applied as an agglomerated cubette at ca. 5 lb/acre.

EXAMPLE 4

A controlled delivery system for solvent-base (i.e., acetone) precipitation was developed to agglomerate an aqueous admixture suspension of a joint-function carrier/coating water soluble polyvinyl alcohol film (MonoSol® 8000 series) and B.t.i. (Acrobe® Biolarvicide). The procedure utilized a series of acetone washes to rapidly congeal the aqueous homogeneous mixture of polyvinyl alcohol film and B.t.i. into a unified mass by removing the water entrapped within the solid. Polyvinyl alcohol films (specific gravity greater than one) are soluble in water and insoluble in acetone while B.t.i. is suspendible in water but insoluble in acetone or water.

Compositions were prepared utilizing the following protocol: 12 g polyvinyl alcohol film (MonoSol® 8000 series) was dissolved in 46.8 g distilled water in a plastic beaker. 1.2 g Acrobe® Biolarvicide was mixed with the water-base joint-function carrier/coating with a GE® 420A hand mixer for ca. 2 minutes. The formulation was poured into 2 ounce glass medicine bottles and vigorously hand shaken for ca. 1 minute. 7 to 10 g polyvinyl alcohol film/B.t.i/water formulation was added to a plastic centrifuge tube (ca. 60 ml capacity) containing ca. 35–40 g acetone. The centrifuge tube was capped and vigorously hand shaken to solidify the polyvinyl alcohol film and B.t.i. into a unified mass within the aqueous-acetone medium. The solid mass was removed and placed into 50 ml glass beakers containing ca. 40 g acetone for a series of five one minute washes to remove entrapped water from within the solid matrix. The solid mass was removed from the acetone and thoroughly air-dried in a low humidity room (ca. 27–38% RH) for ca. 72 hr. The solid compositions were stored in zip-lock (trade mark) bags until bioassay. The remaining stock formulation of water, polyvinyl alcohol film, and B.t.i. was stored in a refrigerator (ca. 40° F.) for future use.

A series of short-term bioassays were conducted against larvae of *Anopheles, Aedes,* and *Culex* species in fresh and brackish water with 2×2×2 mm cubettes that were sectioned from each agglomerated mass of polyvinyl alcohol film and B.t.i. (Table 6). An application rate of one cubette (ca. 0.01 g) per bioassay test chamber (i.e., ½ gal plastic beaker) was extrapolated to be ca. 5 lb/surface acre of water (3 replications/test). Results indicated that 100% control of surface or subsurface feeding larvae could be achieved in fresh or brackish water within 1 to 5 days posttreatment. Based on the specific gravity of the components, cubettes were expected to sink upon introduction to fresh and brackish water. However, observations indicated that the agglomerated polyvinyl alcohol film compositions initially floated and began to solubilize over a 24 hr period, thereby rapidly releasing significant quantities of B.t.i. from the surface to subsurface areas while also retaining B.t.i. in the polyvinyl alcohol film that had spread over the surface of the water. It appears that air bubbles entrapped within the polyvinyl alcohol film matrix during the vigorous admixing procedure in combination with the suspending agents/surfactants present in the Acrobe® Biolarvicide formulation were responsible for the initial surface orientation of the cubettes, and the film-forming properties of the water soluble cubettes. The data on the rates of mortality of surface (i.e., *Anopheles spp.*) and subsurface (i.e., *Aedes* and *Culex spp.*) feeding larvae support the aforementioned observations concerning film-forming solubilization of cubettes and release of B.t.i in the experimental aquatic habitats.

TABLE 6

Example 4. Coating-Regulated Delivery of Acrobe ® Biolarvicide from an Agglomerated Joint-Function Composition*

| Mosquito Species | Larval Instar | Water Quality | % Control of Larvae at Indicated Posttreatment Time Period (Days)** | | | | |
|---|---|---|---|---|---|---|---|
| | | | 1 | 2 | 3 | 4 | 5 |
| Surface Feeders (*Anopheles spp.*) | | | | | | | |
| *An. albimanus* | 2nd | Fresh | 70.0 | 76.7 | 100.0 | — | — |
| *An. albimanus* | 2nd | Brackish | 46.7 | 50.0 | 100.0 | — | — |
| *An. albimanus* | 3rd | Fresh | 40.0 | 46.7 | 90.0 | 100.0 | — |
| *An. albimanus* | 3rd | Brackish | 43.3 | 46.7 | 100.0 | — | — |
| *An. quadrimaculatus* | 2nd | Fresh | 93.3 | 93.3 | 100.0 | — | — |
| *An. quadrimaculatus* | 3rd | Fresh | 30.0 | 30.0 | 66.7 | 90.0 | 100.0 |
| Subsurface Feeders (*Aedes* and *Culex spp.*) | | | | | | | |
| *Ae. taeniorhynchus* | 2nd | Brackish | 100.0 | — | — | — | — |
| *Ae. taeniorhynchus* | 3rd | Brackish | 100.0 | — | — | — | — |
| *Cx. quinquefasciatus* | 2nd | Fresh | 100.0 | — | — | — | — |
| *Cx. quinquefasciatus* | 3rd | Fresh | 100.0 | — | — | — | — |

*9% Acrobe ® Biolarvicide (w/w) in each controlled release B.t.i. composition. Compositions contained a water and solvent-free joint-function carrier/coating polyvinyl alcohol film (91%) and bioactive agent 9%.
**B.t.i. compositions applied as agglomerated cubettes at ca. 5.0 lb/acre.

EXAMPLE 5

A series of short-term controlled release bioassays were also conducted against larvae of *Anopheles*, *Aedes*, and *Culex* species in fresh and brackish water to determine the mosquito-controlling efficacy of powdered compositions comprising admixtures of B.t.i. (Vectobac® TP), the insect growth regulator methoprene (Dianex®EC), a joint-action formulation of Dianex®EC and B.t.i. (Acrobe®TP) or an organophosphate (Abate®4-E) and a cetyl alcohol coating and hydrophobic silica (Sipernat® D17) carrier. Abate® 4-E was also admixed with a water soluble polyvinyl alcohol film (MonoSol® 8000 series) joint-function carrier/coating to form a solid agglomerated composition that was sectioned into cubettes (ca. 3.5×3.5×4.5 mm). Admixing procedures for formulating these powdered or agglomerated controlled delivery compositions are presented in Table 7.

Results of bioassays with the powdered and cubette compositions indicated that controlled delivery of formulations of an organophosphate (specific gravity greater than one), insect growth regular (specific gravity less than one) and a bacteria (specific gravity greater than one)/insect growth regulator (specific gravity less than one) from a hydrophobic silica or joint-function polyvinyl alcohol film carrier was regulated by the physico-chemical characteristics of the cetyl alcohol or polyvinyl alcohol film coatings admixed into the formulation (Table 8). The data indicated that the surface-active powdered or agglomerated (cubette) floating compositions were effective in delivering at varying rates one or more bioactive agents at and/or below the surface of the water where *Anopheles*, *Aedes*, and *Culex* species could be targeted by the specific type(s) of bioactive agent(s) released from the carrier into different vertical and horizontal areas of the water column. One hundred percent control of all immature mosquitoes was observed within 1 to 21 days posttreatment when the compositions were applied as a direct treatment or pretreatment in fresh or brackish water at an extrapolated rate of 2.5 lb/surface acre of water for powdered compositions and 5.0 lb/surface acre of water for agglomerated compositions.

TABLE 7

(Example 5). Formulation Components in Powdered and Agglomerated Controlled Delivery Compositions

| Composition Code | Concentration of Admixtures in Powdered and Agglomerated Compositions |
|---|---|
| Powdered Compositions* | |
| D | 0.5 g methoprene (Dianex ® EC) + 10 g cetyl alcohol + 89.5 g hydrophobic silica (Sipernat ® D17) |
| E | 5 g [0.5 g methoprene (Dianex ® EC) + 10 g cetyl alcohol + 89.5 g hydrophobic silica (Sipernat ® D17)] + 5 g [5 g B.t.i. (Acrobe ® TP) + 10 g cetyl alcohol + 85 g hydrophobic silica (Sipernat ® D17)] |
| F | 5 g B.t.i. (Vectobac ® TP) + 10 g cetyl alcohol + 85 g hydrophobic silica (Supernat ® D17) |
| G | 0.5 g temephos (Abate ® 4-E) + 10 g cetyl alcohol + 89.5 g hydrophobic silica (Sipernat ® D17) |
| Agglomerated Compositions ** | |
| H | 0.3 g temephos (Abate ® 4-E) + 12 g polyvinyl alcohol film (MonoSol ® 8000 series) + 47.7 g distilled water + acetone bath series |

* Cetyl alcohol (heated to 60° C.) was added to 300 g acetone and mixed for ca. 5 minutes with a GE ® Model 420A hand mixer in a 1/2 gal plastic beaker. B.t.i., methoprene or methoprene and B.t.i. or temephos was slowly added to the solvent-base formulations of coating while mixing for an additional 5 minutes. Hydrophobic silica was added to each solvent-base bioactive agent/coating formulation while mixing was continued for ca. 3 hr to drive off the acetone and assurethat the silica was uniformly encapsulated with the homogeneous mixture of each bioactive agent and coating. Two bioactive agents were combined into a single formulation by admixing each bioactive agent/coating/carrier formulation at a 1:1 mixing ratio. Each powdered composition was placed in a low humidity room (ca. 27–38% RH) for ca. 4 hr to assure volatilization of the solvent. The dry powdered compositions were stored in zip-lock bags or glass bottles until being utilized inmosquito bioassays.

TABLE 7-continued (Example 5). Formulation Components in Powdered and
Agglomerated Controlled Delivery Compositions Composition   Concentration of Admixtures in Powdered and
Code          Agglomerated Compositions

** Polyvinyl alcohol film was dissolved in distilled water in a plastic beaker. Temephos was mixed with the aqueous formulation of joint-function coating/carrier with a GE ® Model 420A hand mixer for ca. 2 minutes. The insecticide formulation was poured into 2 ounce glass medicine bottles and vigorous shaken by hand for ca. 1 minute. 7–10 g water-base polyvinyl alcohol film/temephos formulation was added into a plastic centrifuge tube (ca. 60 ml capacity) containing ca.35–40 g acetone. The centrifuge tube was capped and vigorous hand shaken to solidify the polyvinyl alcohol film and B.t.i. admixture into a unified mass within the aqueous-acetone medium. The solid mass was removed and placed into 50 ml glass beakers containing ca. 40 g acetone for a series of five one minute washes to remove entrapped water from within the solid matrix. The solid mass was removed from the acetone and thoroughly air-dried in a low humidity room (ca. 27–38% RH)for ca. 72 hr. The solid compositions were stored in zip-lock bags or glass bottles until being used for mosquito bioassays. Remaining stock formulation of water, polyvinyl alcohol, and temephos was stored in a refrigerator (ca. 40° F.) for future use.

sitions composed of one or more bioactive agents having differential degrees of specific gravity greater than or less than one, one or more coatings having specific gravities with differential degrees of greater than or less than one as well as differential degrees of water solubility or insolubility, and a carrier having hydrophobic or hydrophilic characteristics, with or without a binder component. Carrier components consisted of either a hydrophobic silica (Sipernat® D17) or hydrophilic silica (FK 500 LS or Wesslon™ 50). Bioactive agents utilized in the admixture compositions were B.t.i. (Acrobe® TP), a combination of B.t.i. and methoprene (Dianex® EC) or temephos (Abate® 4-E). Coatings utilized as bioactive agent release rate and release profile regulators were cetyl alcohol (specific gravity less than one/insoluble in water), triethyl citrate (Citroflex® 2; specific gravity greater than one/water soluble), acetyltriethyl citrate (Citroflex® A-2; specific gravity greater than one/water soluble), tributyl citrate (Citroflex® 4; specific gravity greater than one/insoluble in water), acetyltributyl citrate (Citroflex® A-4; specific gravity greater than one/insoluble in water), acetyltri-n-hexyl citrate (Citroflex® A-6; specific gravity greater than one/insoluble in water), n-butyltri-n-hexyl citrate (Citroflex B-6; specific gravity less than one/insoluble in water), dicyclohexyl phthalate (Morflex® 150;

TABLE 8

Example 5. Coating-Regulated Delivery of Dianex ® EC, Dianex ® EC/,
Acrobe ® TP Vectobac ® TP or Abate ® 4-E
from Powdered or Agglomerated Compositions*

| Mosquito Species | Larval Instar | Water Qualtiy | No. Days to Achieve 100% Control of Larvae, Pupae, and/or Emerging Adults |
|---|---|---|---|
| Powdered Composition - Dianex ® EC (0.5% AI Formulation) - Code D | | | |
| An. albimanus | 1st | Fresh | 21** |
| An. albimanus | 1st | Brackish | 20** |
| Ae. aegypti | 3rd | Fresh | 16 |
| Ae. taeniorhynchus | 3rd | Brackish | 14 |
| Powdered Composition - Dinex ® EC/ Acrobe ® TP (0.5%/5% AI 1:1 Formulation) - Code E | | | |
| Ae. taeniorhynchus | 3rd | Brackish | 4 |
| Cx. quinquefasciatus | 3rd | Fresh | 18 |
| Powdered Composition - Vectobac ® TP (5% AI Formulation) - Code F | | | |
| Cx. quinquefasciatus | 2nd | Fresh | 10 |
| Powdered Composition - Abate ® 4-E (0.5% AI Formulation) - Code G | | | |
| An. albimanus | 1st | Fresh | 1 |
| An. albimanus | 1st | Fresh | 2** |
| An. albimanus | 1st | Brackish | 1 |
| An. albimanus | 1st | Brackish | 2** |
| Ae. taeniorhynchus | 3rd | Brackish | 1 |
| Cx. quinquefasciatus | 3rd | Fresh | 1** |
| Agglomerated Composition - Abate ® 4-E (0.5% AI Aqueous/2.4% AI Dry Formulation) - Code H | | | |
| An. albimanus | 4th | Fresh | 1 |
| An. albimanus | 4th | Brackish | 1 |
| An. quadrimaculatus | 4th | Fresh | 1 |
| Ae. taeniorhynchus | 3rd | Brackish | 1 |
| Cx. quinquefasciatus | 2nd | Fresh | 1 |

*Powdered controlled release compositions consisted of a cetyl alcohol coating, bioactive, agent(s), and hydrophobic silica carrier. Agglomerated (cubette) controlled release compositions consisted of a water and solvent-free joint-function poly-vinyl alcohol film coating/carrier (97.6%) and bioactive agent (2.4%). Powdered and agglomerated compositions applied to the water at rates of 2.5 and 5.0 lb/acre, respectively.
**Presoaked (pretreatment) in water for 9 days before transfer to bioassay containers.

EXAMPLE 6

A series of long-term controlled release transfer-bioassays were conducted against multiple broods of larvae of *Anopheles*, *Aedes*, and *Culex* species in fresh or brackish water with a variety of powdered or agglomerated compospecific gravity greater than one/insoluble in water), butyl phthalyl butyl glycolate (Morflex® 190; specific gravity greater than one/insoluble in water), and tri-n-hexyl trimellitate (Morflex® 560; specific gravity greater than one/insoluble in water). Binders admixed with selected formulations to assist in agglomerating the fine components into larger units (e.g., briquets) were either a sulfonated polystyrene polymer (Versa® TL-502), a sulfonated vinylic copolymer (Narlex® D-82) or a water soluble starch. Components utilized in the admixing procedures to formulate the controlled release compositions are presented in Table 9.

Results of a series of long-term transfer bioassays in fresh and brackish water against several broods of larvae of *Anopheles, Aedes,* and *Culex* species with a variety of powdered and agglomerated (i.e., cubette) compositions of B.t.i. (Acrobe® TP) or methoprene (Dianex® EC) and B.t.i. have indicated that these controlled release compositions can be effective in slowly distributing lethal concentrations of a bacteria and/or insect growth regulator for a prolonged period to surface and/or subsurface areas of a water column that were readily accessible to the feeding and/or orientation of various species of larvae (Table 10). The data indicated that the direction(s), duration, and rate(s) of controlled release of the bioactive agent(s) in an aquatic habitat were functions of the surface or subsurface orientation of the carrier(s), and the type and concentration of coating(s) and bioactive agent(s) utilized in the powdered or agglomerated compositions. The results indicated that 100 % control of multiple broods of larvae of *Anopheles, Aedes* or *Culex* species could be obtained in fresh or brackish water for at least 3–8 weeks when powdered or agglomerated compositions were applied to the water at rates of ca. 2.5 and 5.0 lb/acre, respectively. Powdered and agglomerated compositions were still producing 100% control of larval populations when tests were terminated.

TABLE 9

(Example 6). Formulation Components in Powdered and Agglomerated Controlled Delivery Compositions

| Composition Code/No. | Concentration of Admixtures in Powdered and Agglomerated Compositions |
|---|---|
| Powdered Compositions* | |
| J (Example 1) | 5 g [5 g B.t.i. (Acrobe ® TP) + 10 g cetyl alcohol + 85 g hydrophobic silica (Sipernat ® D17)]+ 5 g [5 g B.t.i. (Acrobe ® TP) + 5 g triethyl citrate (Citroflex ® 2) + 90 g hydrophobic silica (Sipernat ® D17)] |
| 2 (Example 2) | 5 g B.t.i. (Acrobe ® TP) + 10 g cetyl alcohol + 85 g hydrophilic silica (FK 500 LS) |
| K | 5 g B.t.i. (Acrobe ® TP) + 5 g triethyl citrate (Citroflex ® 2) + 90 g hydrophilic silica (Wesslon ™ 50) |
| L | 5 g B.t.i. (Acrobe ® TP) + 5 g acetyltriethyl citrate (Citroflex ® A-2) + 90 g hydrophilic silica (Wesslon ™ 50) |
| M | 5 g B.t.i. (Acrobe ® TP) + 5 g tributyl citrate (Citroflex ® 4) + 90 g hydrophilic silica (Wesslon ™ 50) |
| N | 5 g B.t.i. (Acrobe ® TP) + 5 g triethyl citrate (Citroflex ® 2) + 90 g hydrophobic silica (Sipernat ® D17) |
| O | 5 g B.t.i. (Acrobe ® TP) + 5 g acelytriethyl citrate (Citroflex ® A-2) + 90 g hydrophobic silica (Sipernat ® D17) |
| P | 5 g B.t.i. (Acrobe ® TP) + 5 g tributyl citrate (Citroflex ® 4) + 90 g hydrophobic silica (Sipernat ® D17) |
| Q | 5 g B.t.i. (Acrobe ® TP) + 5 g acetyltributyl citrate (Citroflex ® A-4) + 90 g hydrophobic silica (Sipernat ® D17) |
| R | 5 g B.t.i. (Acrobe ® TP) + 5 g acetyltri-n-hexyl citrate (Citroflex ® A-6) + 90 g hydrophobic silica (Sipernat ® D17) |
| S | 5 g B.t.i. (Acrobe ® TP) + 5 g n-butyltri-n-hexyl citrate (Citroflex ® B-6) + 90 g hydrophobic silica (Sipernat ® D17) |

TABLE 9-continued (Example 6). Formulation Components in Powdered and Agglomerated Controlled Delivery Compositions

| Composition Code/No. | Concentration of Admixtures in Powdered and Agglomerated Compositions |
|---|---|
| T | 5 g B.t.i. (Acrobe ® TP) + 2.5 g triethyl citrate (Citroflex ® 2) + 2.5 g tributyl citrate (Citroflex ® 4) + 90 g hydrophobic silica (Sipernat ® D17) |
| U | 5 g B.t.i. (Acrobe ® TP) + 5 g dicyclohexyl phthalate (Morflex ® 150) + 90 hydrophobic silica (Sipernat ® D17) |
| V | 5 g B.t.i. (Acrobe ® TP) + 5 g butyl phthalyl butyl glycolate (Morflex ® 190) + 90 g hydrophobic silica (Sipernat ® D17) |
| W | 5 g B.t.i. (Acrobe ® TP) + 5 g tri-n-hexyl trimellitate (Morflex ® 560) + 90 g hydrophobic silica (Sipernat ® D17) |
| E (Example 5) | 5 g [5 g B.t.i. (Acrobe ® TP) + 10 g cetyl alcohol + 85 g hydrophobic silica (Sipernat ® D17)]+ 5 g [0.5 g methoprene (Dianex ® EC) + 10 g cetyl alcohol + 89.5 g hydrophobic silica (Sipernat ®D17)] |
| Agglomerated Compositions** | |
| A (Example 3) | 5 g (5 g B.t.i. (Acrobe ® TP) + 10 g cetyl alcohol + 85 g hydrophobic silica (Sipernat ® D17)]+ 5 g sulfonated polystyrene polymer (Versa ® TL-502) |
| B (Example 3) | 5 g (5 g B.t.i. (Acrobe ® TP) + 10 g cetyl alcohol + 85 g hydrophobic silica (Sipernat ® D17)]+ 5 g sulfonated vinylic copolymer (Narlex ® D-82) |
| C (Example 3) | 5 g [5 g B.t.i. (Acrobe ® TP) + 10 g cetyl alcohol + 85 g hydrophobic silica (Sipernat ® D17)]+ 5 g soluble starch |

* Cetyl alcohol (heated to 60° C.), triethyl citrate, a combination of triethyl citrate and cetyl alcohol, acetyltriethyl citrate, tributyl citrate, acetyltributyl citrate, acetyltri-n-hexyl citrate, n-butyltri-n-hexyl citrate, dicyclohexyl phthalate, butyl phthalyl butyl glycolate, tri-n-hexyl trimellitate, or a 1:1 combination of triethyl citrate and tributyl citrate was added to 300 g acetone and mixed for ca. 5 minutes (speed #6; wire whip) with a KitchenAid ® KSM90 hand mixerin a 4 1/2 qt stainless steel bowl or with a GE ® hand mixer Model 420A. B.t.i. or a B.t.i. and methoprene mixture was slowly added to the solvent-base formulations of coatings while mixing (stir, speed #6, wire whip) was continued for ca. 5 minutes. Hydrophobic or hydrophilic silica was added to each solvent-base bioactive agent/coating formulation while mixing (stir, speed #6, wire whip, flat beater blade) was continued for ca. 3 hr to drive office the acetone and assurethat the silica was uniformly encapsulated with the homogeneous mixture of each bioactive agent and coating. Two bioactive agents were combined into a single formulation by admixing each bioactive agent/coating/carrier formulation at a 1:1 mixing ratio. Each powdered composition was placed in a low humidity room (ca. 27–38% RH) for ca. 3 to 4 hr to assure volatilization of the solvent. The dry powdered compositions were stored in zip-lock bags or glass bottles until being utilized inmosquito bioassays.
** Cetyl alcohol (heated to 60° C.) was added to 300 g acetone and mixed for ca. 5 minutes with a GE ® Model 420A hand mixer in a 1/2 gal plastic beaker. B.t.i. was slowly added into the solvent-base formulation of coating while mixing for an additional 5 minutes. Hydrophobic silica was mixed with the other components while mixing was continued for ca. 3 hr to drive off the acetone and assure a homogeneous dry mixture of all components. The powdered composition wasplaced in a low humidity room (ca. 27–38% RH) for ca. 4 hr to assure volatilization of solvent. A ratio of one part of this powdered 3-part bioactive agent/coating/carrier formulation was mixed with one part binder (sulfonated polystyrene polymer, sulfonated vinylic copolymer or soluble starch) for ca. 5 minutes. The 1:1 composition was then hand compacted into 25 × 20 × 5 mm vinyl specimen molds (Cryomold ®) and placed in a high humidity curing room (ca. 80% RH and80° F.) for ca. 96 hr. Molds containing each composition were then transferred to a drying room (ca. 27–38% RH, 76–79° F.) for an additional 96 hr. The dry solidified briquet compositions in each mold were stored in plastic zip-lock bags. Subsections of each briquet (i.e., ca. 3.5 × 3.5 × 4.5 mm cubettes) were utilized in the bioassays. One cubette (ca. 0.01 g) was utilized against mosquito larvae in each bioassay test chamber (3 replications/agglomeratedcomposition).

TABLE 10

Example 6. Coating-Regulated Controlled Delivery of Acrobe ® TP or Acrobe ® TP/
Dianex ® EC from Powdered or Agglomerated Compositions*

| Mosquito Species | Larval Instar/ Composition Transfer Period (T)** | Water Quality | Composition Code/No. | No. Days to Achieve 100% Larval Control at Composition Transfer Period (No. Days Between Transfers) | | | | | Test Duration (Days)*** |
|---|---|---|---|---|---|---|---|---|---|
| | | | | $T_0$ | $(T_0{\rightarrow}T_1)$ | $T_1$ | $T_1{\rightarrow}T_2$ | $T_2$ | |
| Powdered Compositions - ACROBE ® TP (5% AI Formulation) | | | | | | | | | |
| Ae. aegypti | 3rd/$T_0$, $T_1$ | Fresh | J | 3 | (31) | 6 | — | — | 40 |
| Ae. taeniorhynchus | 3rd/$T_0$, 1st/$T_1$ | Brackish | 2**** | 1 | (14) | 4 | — | — | 31 |
| Ae. taeniorhynchus | 2nd/$T_0$, $T_1$ | Brackish | K***** | 7 | (15) | 9 | — | — | 61 |
| Ae. taeniorhynchus | 2nd/$T_0$, $T_1$ | Brackish | L***** | 2 | (20) | 4 | — | — | 56 |
| Ae. taeniorhynchus | 2nd/$T_0$, $T_1$ | Brackish | M***** | 2 | (20) | 9 | — | — | 61 |
| An. albimanus | 2nd/$T_0$, $T_1$ | Fresh | N | 3 | (17) | 5 | — | — | 25 |
| An. albimanus | 2nd/$T_0$, $T_1$ | Fresh | O | 1 | (19) | 1 | — | — | 21 |
| An. albimanus | 2nd/$T_0$, $T_1$ | Fresh | P | 1 | (19) | 4 | — | — | 24 |
| An. albimanus | 2nd/$T_0$, $T_1$ | Fresh | Q | 1 | (19) | 2 | — | — | 22 |
| An. albimanus | 2nd/$T_0$, $T_1$ | Fresh | R | 1 | (19) | 1 | — | — | 21 |
| An. albimanus | 2nd/$T_0$, $T_1$ | Fresh | S | 2 | (18) | 1 | — | — | 21 |
| An. albimanus | 2nd/$T_0$, $T_1$ | Fresh | T | 1 | (19) | 1 | — | — | 21 |
| An. albimanus | 2nd/$T_0$, $T_1$ | Fresh | U | 1 | (19) | 1 | — | — | 21 |
| An. albimanus | 2nd/$T_0$, $T_1$ | Fresh | V | 1 | (19) | 3 | — | — | 23 |
| An. albimanus | 2nd/$T_0$, $T_1$ | Fresh | W | 1 | (19) | 1 | — | — | 21 |
| An. albimanus | 2nd/$T_0$, $T_1$ | Brackish | N | 3 | (17) | 8 | — | — | 28 |
| An. albimanus | 2nd/$T_0$, $T_1$ | Brackish | O | 1 | (19) | 10 | — | — | 30 |
| An. albimanus | 2nd/$T_0$, $T_1$ | Brackish | P | 1 | (19) | 15 | — | — | 35 |
| An. albimanus | 2nd/$T_0$, $T_1$ | Brackish | Q | 1 | (19) | 6 | — | — | 26 |
| An. albimanus | 2nd/$T_0$, $T_1$ | Brackish | R | 1 | (19) | 2 | — | — | 22 |
| An. albimanus | 2nd/$T_0$, $T_1$ | Brackish | S | 1 | (19) | 7 | — | — | 27 |
| An. albimanus | 2nd/$T_0$, $T_1$ | Brackish | T | 1 | (19) | 1 | — | — | 21 |
| An. albimanus | 2nd/$T_0$, $T_1$ | Brackish | U | 10 | (10) | 8 | — | — | 28 |
| An. albimanus | 2nd/$T_0$, $T_1$ | Brackish | V | 1 | (19) | 5 | — | — | 25 |
| An. albimanus | 2nd/$T_0$, $T_1$ | Brackish | W | 1 | (19) | 2 | — | — | 22 |
| Powdered Compositions - ACROBE ® TP (5% AI Formulation) | | | | | | | | | |
| Cx. quinquefasciatus | 2nd/$T_0$, $T_1$ | Fresh | K | 2 | (17) | 7 | (26) | 13 | 65 |
| Cx. quinquefasciatus | 2nd/$T_0$, $T_1$ | Fresh | L | 1 | (18) | 14 | (19) | 14 | 66 |
| Cx. quinquefasciatus | 2nd/$T_0$; $T_1$ | Fresh | M | 2 * | (17) | 5 | (28) | 17 | 69 |
| Powdered Compostions - ACROBE ® TP/DIANEX ® EC (5%/0.5% AI 1:1 Formulation) | | | | | | | | | |
| Ae. taeniorhynchus | 3rd/$T_1$, $T_2$ | Brackish | E | 4 | (17) | 13 | — | — | 34 |
| Agglomerated Compositions - ACROBE ® TP (5% AI Formulation) | | | | | | | | | |
| An. albimanus | 2nd/$T_0$, $T_1$; 1st/$T_2$ | Fresh | A | 2 | (12) | 3 | (21) | 9 | 47 |
| An. albimanus | 2nd/$T_0$, $T_1$; 1st/$T_2$ | Fresh | B | 1 | (13) | 3 | (21) | 8 | 46 |
| An. albimanus | 2nd/$T_0$, $T_1$; 1st/$T_2$ | Fresh | C | 9 | (05) | 4 | (20) | 7 | 45 |
| An. albimanus | 2nd/$T_0$, $T_1$; 1st/$T_2$ | Brackish | A | 2 | (12) | 8 | (16) | 1 | 53 |
| An. albimanus | 2nd/$T_0$, $T_1$; 1st/$T_2$ | Brackish | B | 2 | (12) | 3 | (21) | 16 | 54 |
| An. albimanus | 2nd/$T_0$, $T_1$; 1st/$T_2$ | Brackish | C | 7 | (07) | 1 | (23) | 18 | 56 |

*Powdered and agglomerated controlled release compositions of Acrobe ® TP or Acrobe ® TP/Dianex ® EC applied at rates of ca 5.0 lb/acre, respectively.
**$T_0$ = Initial composition introduction;
$T_{1,2}$ = No. post-introduction composition transfers.
***Compositions remained in water for test duration as a pretreatment without larvae or during larvae challenges in $T_0$, $T_1$, and $T_2$, and between transfer periods $T_0$–$T_2$ with dead larvaelpupae. Compositions briefly removed with a 100 mesh sieve to transfer formulations from $T_0$, to $T_1$ and $T_1$ to $T_2$ test chambers. Tests terminated even though compositions were still effective in producing 100% control of immatures.
****Powdered compositions initially introduced into water for 12 days without larvae (pretreatment) before being transferred into $T_0$ test chamber with larvae.
*****Powdered compositions initiaily introdueed into water for 30 days without larvae (pretreatment) before being transferred into $T_0$ test chamber with larvae.

EXAMPLE 7

A series of short-term bioassays were conducted in fresh or brackish water against larvae of *Anopheles*, *Aedes*, and/or *Culex* species with controlled release compositions comprising admixtures of the insect growth regulator methoprene (Dianex®EC), the bacteria B.t.i. (Acrobe® TP) or an experimental monomolecular surface film (POE(2) Isostearyl Alcohol), one or more hydrophobic (FK 500 LS, Sipernat® 22S, Wesslon™) and/or hydrophobic (Sipernat® D17) silica or hydrophobic "pin chips" (SeaSweep®) carriers, and one or more cetyl alcohol (specific gravity less than one, insoluble in water), triethyl citrate (Citroflex®2; specific gravity greater than one, soluble in water), tributyl citrate (Citroflex®4; specific gravity greater than one, insoluble in water), and/or n-butyryl tri-n-hexyl citrate (Citroflex® B-6; specific gravity less than one, insoluble in water) coatings, and/or one or more joint-function polyvinyl alcohol films (specific gravity greater than one, soluble in water) that can act as a coating and carrier. All coatings showed differential surface spreading potentials when applied to the water. Specific formulation components for each of the compositions utilized in these bioassays are presented in Table 11.

Results of larval bioassays against single or mixed species populations indicated that the initial orientation of delivery of an insect growth regulator, bacteria or monomolecular surface film from a controlled delivery composition was dictated by the surface and/or subsurface characteristics of the bioactive agent/coating-encapsulated carrier(s) in an aquatic habitat (Table 12). Changes over time in the initial orientation or direction and rate of delivery in a water column were determined by the specific gravity, solubility, and film-forming characteristics of the coating agent(s) and bioactive agent(s) encapsulated on the carrier(s).

The data indicated that 100% larval control of mixed populations of *Anopheles* and *Culex* species occurred in all powdered B.t.i. formulations (2.5 lb/acre application) in 24 hr posttreatment; however, the rates of control within the 24 hr period were observed to be formulation (i.e., coating) dependent. Complete control (i.e., 100%) of larvae of Aedes with two powdered compositions of POE(2) Isostearyl Alcohol (5 lb/acre application) was observed in 11 and 13 days posttreatment while 100% control of larvae of *Culex* mosquitoes exposed to two "pin chip" compositions of methoprene (2.5 lb/acre application) was observed in 28 and 30 days posttreatment. Mixed populations of *Anopheles* larvae were killed in both water qualities within 24 hr posttreatment with all polyvinyl alcohol film compositions. These agglomerated admixture formulations (i.e., cubettes) initially floated and differentially solubilized within 24 hr. It appears that air entrapped within the polyvinyl alcohol matrices caused the formulations to float. Cubette agglomeration and hardness were affected by the type of solvent utilized in the fabrication process. Polyvinyl alcohol film(s) and B.t.i. compositions (Codes 12, 13, 14) were secondarily admixed with 0.15–0.5 g soluble starch, Carboset® 514H, Carbopol® ETD 2001, Narlex®D-82, Versa® TL-502, Citroflex® A-2, Morflex® 150, FK 500 LS, Sipernat® D17, ethoxylated alcohols, and/or salts (e.g., NaCl Instant Ocean®). Additions of one or more binder, coating agents, carriers, and/or additional ingredients to the formulations indicated in Codes 12, 13, 14 were observed to significantly affect component dissociation from the cubettes as well as the surface/subsurface orientation of the cubettes/cubette components in the water column. The type of salt(s) utilized in the aqueous formulation and the type of solvent(s) utilized in the aqueous agglomeration and drying protocols were observed to have a significant affect on the agglomeration performance and rigidity of the matrices containing the additional admixture ingredients.

TABLE 11

(Example 7). Formulation Components in Powdered, Chipped or Agglomerated Controlled Delivery Compositions

| Composition No. | Concentration of Admixtures in Powdered and Chipped Compositions |
|---|---|
| | Powdered Compositions* |
| 5 | 10 g B.t.i. (Acrobe ® TP) + 20 g cetyl alcohol + 85 g hydrophobic silica (Sipernat ® D17)]+ 85 g hydrophilic silica (Wesslon ™) |
| 6 | 10 g B.t.i. (Acrobe ® TP) + 10 g cetyl alcohol + 10 g triethyl citrate (Citroflex ® 2) + 85 g hydrophobic silica (Sipernat ® D17) and 85 g hydrophilic silica (Wesslon ™) |
| 7 | 10 g B.t.i. (Acrobe ® TP) + 10 g cetyl alcohol + 10 g n-butyrltri-n-hexyl citrate (Citroflex ® B-6) + 85 g hydrophobic silica (Sipernat ® D17) + 85 g hydrophilic silica (Wesslon ™) |
| 8 | 24.75 g Monomolecular Surface Film (POE(2) Isostearyl Alcohol) + 0.25 g triethyl citrate (Citroflex ® 2) + 75 g hydrophilic silica (Sipernat ® 22S) |

TABLE 11-continued (Example 7). Formulation Components in Powdered, Chipped or Agglomerated Controlled Delivery Compositions

| Composition No. | Concentration of Admixtures in Powdered and Chipped Compositions |
|---|---|
| 9 | 24.75 g Monomolecular Surface Film POE(2) Isostearyl Alcohol) + 0.25 g tributyl citrate (Citroflex ® 4) + 75 g hydrophilic silica (Sipernat ® 22S) |
| | Chipped Compositions** |
| 10 | 5 g methoprene (Dianex ® EC) + 5 g triethyl citrate (Citroflex ® 2) + 90 g "pin chips" (SeaSweep ®) |
| 11 | 5 g methoprene (Dianex ® EC) + 5 g n-butyrltri-n-hexyl citrate (Citroflex ® B-6) + 90 g "pin chips" (Seasweep ®) |
| | Agglomerated Compositions*** |
| 12 | 3 g B.t.i. (Acrobe ® Biolarvicide) + 12 g polyvinyl alcohol film (MonoSol ® 8000 series) + 45 g distilled water + acetone, methyl ethyl ketone or 2-propanol bath series |
| 13 | 3. g B.t.i. (Acrobe ® Biolarvicide) + 12 g polyvinyl alcohol film (MonoSol ® 7000 series) + 45 g distilled water + acetone, methyl ethyl ketone or 2-propanol bath series |
| 14 | 3 g B.t.i. (Acrobe ® Biolarvicide) + 6 g polyvinyl alcohol film (MonoSol ® 8000 series) + 6 g polyvinyl alcohol film (MonoSol ® 7000 series) + 45 g distilled water + acetone, methyl ethyl ketone or 2-propanol bath series |

* Cetyl alcohol (heated to 60° C.), triethyl citrate, tributyl citrate, and/or n-butyrltri-n-hexyl citrate was added to 600 g acetone and mixed for ca. 5 minutes (speed #6, wire whip) with a KitcheAid ® KSM 90 hand mixer in a 4 1/2 qt stainless steel bowl. B.t.i. or the experimental monomolecular surface film was slowly added to the solvent-base formulations of coatings while mixing (stir, speed #6, wire whip) was continued for ca. 5 minutes. Hydrophobic and/orhydrophilic silica was added to each solvent-base bioactive agent/coating formulation while mixing (stir, speed #6, wire whip, flat beater blade) was continued for ca. 3 hr to drive off the acetone and assure that each silica was uniformly encapsulated with the homogeneous mixture of each bioactive agent and coating(s). Each powdered composition was placed in a low humidity room (ca. 27–38% RH) for ca. 3 to 4 hr to assure volatilization of the solvent. The dry powdered compositionswere stored in zip-lock bags or glass bottles until being utilized in mosquito bioassays.
**Triethyl citrate or n-butyrltri-n-hexyl citrate and methoprene were added to 300 g acetone in 1000 ml Nalgene bottles and placed on a paint shaker (Miller Strokemaster ™) for ca. 1 hr to assure that the insect growth regulator formulation was well mixed. "Pin chips" (ca. 2 × 8 mm) were added to the bottles containing the acetone/methoprene/citrate formulations and hand shaken for ca.10–30 seconds to assure that the "pin chips" were saturated with the formulations. "Pin chips" continued to soak in the formulations for ca. 18 hr before being removed on sieves and placed in a drying room (ca. 27–38% RH) for ca. 24 hr to assure volatilization of the acetone. The dry "pin chip" formulations were placed into zip-lock bags until being used for mosquito bioassays.
*** One or more polyvinyl alcohol films were dissolved in distilled water in a plastic beaker. B.t.i. was mixed with the aqueous formulation of joint-function coating/carrier with a KitchenAid ® KSM 90 hand mixer for ca. 1 to 2 minutes. The insecticide formulations were poured into 2 ounce glass medicine bottles and vigorously shaken by hand for ca. 1 minute. 7–10 g water-base polyvinyl alcohol films/B.t.i. formulations were added to plastic centrifuge tubes (ca. 60 mlcapacity) containing ca. 35–40 g acetone, methyl ethyl ketone or 2 propanol. The centrifuge tube was capped and vigorously hand shaken to solidify to polyvinyl alcohol film(s) and B.t.i. admixtures into a unified mass within the aqueous-acetone, aqueous-methyl ethyl ketone or aqueous-2-propanol medium. The solid mass from each tube was removed and placed into 50 ml glass beakers containing ca. 40 g acetone, methyl ethyl ketone or 2-propanol for a series of five one minute washes toremove entrapped water from the solid matrix. The solid mass was removed from each acetone, methyl ethyl ketone or 2-propanol bath and thoroughly air-dried in a low humidity room (ca. 27–38% RH) for ca. 72 hr. The solid compositions were stored in zip-lock bags or glass bottles until being used for mosquito bioassays. Remaining stock formulations of water, polyvinyl alcohol film(s), and B.t.i. were stored in a refrigerator (ca. 40° F.) for future. use.

TABLE 12

Example 7. Coating-Regulated Delivery of Acrobe ® TP, Dianex ® EC or POE(2)
Isostearyl Alcohol from Powdered, Chipped or Agglomerated Compositions

| Mosquito Species | Larval Instar | Water Quality | Composition No. | No. Days to Achieve 100% Control of Larvae, Pupae and/or Emerging Adults |
|---|---|---|---|---|
| Powdered Composition - Acrobe ® TP (5% AI Formulation)* | | | | |
| An. albimanus/ Cx. quinquefasciatus | 2nd/ 2nd | Fresh | 5 | 1 |
| An. albimanus/ Cx. quinquefasciatus | 2nd/ 2nd | Fresh | 6 | 1 |
| An. alhimanus/ Cx. quinquefasciatus | 2nd/ 2nd | Fresh | 7 | 1 |
| An. albimanus/ Cx. quinquefasciatus | 2nd/ 2nd | Brackish | 5 | 1 |
| An. albimanus/ Cx. quinquefasciatus | 2nd/ 2nd | Brackish | 6 | 1 |
| An. albimanus/ Cx. quinquefasciatus | 2nd/ 2nd | Brackish | 7 | 1 |
| Powdered Compositions - POE(2) Isostearyl Alcohol (25% AI Formulation)** | | | | |
| Ae. taeniorhynchus | 3rd | Brackish | 8 | 11 |
| Ae. taeniorhynchus | 3rd | Brackish | 9 | 13 |
| Chipped Compositions - Dianex ® EC (5% AI Formulation)*** | | | | |
| Cx. quinquefasciatus | 2nd | Fresh | 10 | 26 |
| Cx. quinquefasciatus | 2nd | Fresh | 11 | 23 |
| Agglomerated Compositions - Acrobe ® TP (20% AI Formulation)**** | | | | |
| An. albimanus | 2nd | Fresh | 12 | 1 |
| An. albimanus | 2nd | Fresh | 13 | 1 |
| An. albimanus | 2nd | Fresh | 14 | 1 |
| An. albimanus | 2nd | Brackish | 12 | 1 |
| An. albimanus | 2nd | Brackish | 13 | 1 |
| An. albimanus | 2nd | Brackish | 14 | 1 |

*Powdered controlled delivery compositions of B.t.i., one or more cetyl alcohol and/or citrate coatings, and one or more hydrophobic and/or hydrophilic silica carriers were applied at a rate of ca. 2.5 lb/acre (i.e., 0.005 g/bioassay test chamber).
**Powdered controlled delivery compositions of a monomolecular surface film, a citrate coating, and a hydrophilic silica carrier were applied at a rate of ca. 5 lb/acre (i.e., 0.01 g/bioassay test chamber).
***Chipped controlled delivery compositions of methoprene, a citrate coating, and a hydrophobic "pin chip" carrier were applied at a rate of ca. 2.5 lb/acre (i.e., 5 "pin chips"; 0.005 g/bioassay test chamber).
****Agglomerated controlled delivery compositions (i.e., cubettes) of B.t.i. (20%) and a water and solvent-free joint-function polyvinyl alcohol film coating/carrier (80%) were applied at a rate of ca. 5 lb/acre (i.e., one, 0.01 g cubette/bioassay test chamber). Aqueous insecticide formulations fabricated into solid mass by a series of solvent precipitation and evaporation procedures.

EXAMPLE 8

In another evaluation, 0.01, 0.05, and 0.1 g Pemulen® TR-1 or Pemulen® TR-2 acrylic copolymer suspending agents were added to 47.5 g distilled water in 50 ml glass medicine bottles and vigorously shaken by hand for ca. 2–3 minutes to form a homogeneous mixture. 2.5 g of the powdered controlled release compositions of B.t.i. (Acrobe® TP), one or more hydrophobic and/or hydrophilic silica carriers and one or more Citroflex®, Morflex® and/or cetyl alcohol coatings (Examples 1–7) were added to each of the aqueous acrylic copolymer formulations and placed on a mechanical shaker and vigorously mixed for ca. 5 minutes to assure that the silica-base compositions were uniformly suspended throughout the water column. Results of the suspendability tests indicated that these powdered compositions could be readily dispensed in water with conventional spray equipment. Suspension of compositions in petroleum or nonpetroleum oils for spray application is also proposed.

EXAMPLE 9

In another test, an aqueous formulation of the aquatic herbicide Aquathol®K (dipotassium salt of endothall) was admixed with a joint-function (carrier/coating) polyvinyl alcohol film (MonoSol® 8000 series, M-7030, M-8533 or M-8030) and agglomerated into a solidified controlled delivery mass in a series of solvent precipitation and evaporation procedures. The admixing protocol utilized was similar to procedures described in Examples 4, 5, and 7. As indicated in the earlier examples, polyvinyl alcohol film (specific gravity greater than one) is soluble in water (temperature dependent) but insoluble in most organic and inorganic solvents, hydrocarbons or oils. These properties are also similar for polyethylene oxide and hydroxypropyl methyl cellulose water-soluble films. MonoSol® 8000 series was obtained from the manufacturer as solid sheets/pouches and dissolved in water (20% polyvinyl alcohol film) while MonoSol® M-7030, M-8533 and M-8030 were obtained as water-base solutions (16.1–16.4% polyvinyl alcohol film).

The following formulations were utilized in fabricating the joint-function polyvinyl alcohol compositions of Aquathol®K: Composition AK1—4 g dipotassium salt of endothall (Aquathol®K)+12.5 g polyvinyl alcohol film (MonoSol® 8000 series)+46 g distilled water+acetone bath series; Composition AK2—2. g dipotassium salt of endothall (Aquathol®K)+7.4 g polyvinyl alcohol film (MonoSol® M-7030)+40.6 g distilled water+acetone bath series; Composition AK3—2 g dipotassium salt of endothall (Aquathol®K)+7.3 g polyvinyl alcohol film (MonoSol® M-8533)+40.7 distilled water+acetone bath series; and Composition AK4—2 g dipotassium salt of endothall (Aquathol®K)+7.3 g polyvinyl alcohol film (MonoSol® M-8030)+40.7 g distilled water+acetone bath series.

The dried agglomerated briquet compositions of AK1, AK2, AK3, and AK4 consisted of 24.4, 21.5, 21.7, and 21.8% (w/w) dipotassium salt of endothall, respectively. Commercial Aquathol®K granules contain only 10.1% dipotassium salt of endothall.

Results of the admixing procedures indicated that high levels of Aquathol®K can be agglomerated into solid polyvinyl alcohol-base compositions for fast-release application into an aquatic habitat for control of nuisance vegetation. All compositions solubilized in fresh water within 2 hr of introduction-and showed differential degrees of floating or sinking depending on the type and/or concentration of polyvinyl alcohol utilized in the formulation.

Loading levels were significantly higher than the standard commercially available granular Aquathol®K product (i.e., 10.1% dipotassium salt of endothall), and therefore, a lesser amount (on a weight basis) per acre of MonoSol®/Aquathol®K would be required to treat an acre of aquatic weeds when compared to the amount or weight of conventional Aquathol®K granular product needed per acre to be equivalent to the concentration of dipotassium salt of endothall in the composition. The results indicated that significantly higher loading levels can be obtained with the polyvinyl alcohol-base protocol. Addition of one or more coatings, surfactants, binders, and the like is expected to change the controlled release profiles of the compositions. Any herbicide can be fabricated into a solid controlled delivery composition utilizing the joint-function polyvinyl alcohol-base admixing protocol.

The foregoing coating components, bioactive agents and carrier components can be selected to control or eliminate various terrestrial organisms, and especially nuisance plant and animal organisms such as weeds, rodents and insects, including but not limited to cockroaches, ants, fire ants, termites, and other varieties of biting insects, disease carrying insects, crop eating insects, and wood eating insects. The coatings that are selected in this regard are the degradable ones, e.g. biodegradable coatings selected from those listed above, and those that also will protect the bioactive agent from degradation, especially ultraviolet light degradation. The coatings are also selected to release the bioactive agent over a period of time so as to increase the effectiveness of the bioactive agent.

The compositions of the invention can also be utilized in the treatment of parasitic or insect caused diseases in animals, especially the G.I. tract of animals such as ruminants, by selecting those components of the composition that are approved for animal use. When properly administered they can be employed to provide time release compositions for the treatment of various diseases and disorders. Non-bioactive compounds or compositions can be used in lieu of the bioactive agents for the treatment of certain disorders such as the treatment of hoven in ruminants by means of surfactant silicone compounds. Some non-limiting examples of other compounds that may be used in the treatment of animals is disclosed by Drummond et al., *Control of Arthropod Pests of Livestock: A Review of Technology,* 1988, CRC Press, Inc. which is incorporated herein by reference.

In the course of preparing the various compositions of the invention it was further discovered that in many instances the materials employed as coatings, carriers, and binders were interchangeable. Joint-function carrier coating materials have been described, but in the broader aspects of the invention, the coating, carrier, and binder compounds or compositions are to be categorized primarily by the way they are employed in the composition i.e. by the way the function because of the interchangeability of the various compounds and compositions that are useable in this regard.

The principles, preferred embodiments, and modes of operation of the present invention have been described in the foregoing specification. The invention which is intended to be protected here, however, is not to be construed as limited to the particular forms disclosed, since these are to be regarded as illustrative rather than restrictive. Variations and changes may be made by those skilled in the art without departing from the spirit of the invention.

What I claim is:

1. A process for treating a population of one or more aquatic organisms in a column of water by delivering to preflood or flood area a composition of matter consisting essentially of a controlled delivery system for treating a population of one or more aquatic organisms in a column of water which consists essentially of from about 50% to about 99% by weight of a carrier component, from about 0.0001% to about 50% by weight of a bioactive agent for treating a population of one or more aquatic organisms, and from about 1.0% to about 50% by weight of a coating component for regulating the controlled release rate and release profile of said bioactive agent in water, wherein said coating component is water soluble or biodegradable or erodible, and consists essentially of fatty alcohols, fatty acids, and esters thereof, or phthalyl esters, and combinations thereof, and optionally a binder, and wherein said composition is free of superabsorbent polymers.

2. A process for treating a population of one or more aquatic organisms in a column of water, by delivering to a preflood or flood area a composition of matter consisting essentially of a complex for treating a population of one or more aquatic organisms in a column of water, said complex consisting essentially of at least one controlled delivery system consisting essentially of from about 50% to about 99% by weight of at least one carrier component, from about 0.0001% to about 50% by weight of at least one bioactive agent as a component selected for treating a population of one or more aquatic organisms, and from about 1.0% to about 50% by weight of at least one coating component for regulating the controlled release rate and release profile of said bioactive agent in water, wherein said coating component is water soluble or biodegradable or erodible and consists essentially of polyvinyl alcohol, polyethylene oxide, hydroxypropyl methyl cellulose or fatty alcohols, fatty acids, and esters thereof, or phthalyl esters, and combinations thereof, and optionally a binder, and wherein said composition is free of superabsorbent polymers, said components being selected to sink or float so that said complex will permeate and remain in any planar or volumetric segment of a water column for a period of time sufficient to effectively treat a population of one or more aquatic organisms.

3. The process of claim 1 or 2 wherein one of said components is selected to sink, one of said components is selected to float, and the remaining component selected to sink or float.

4. The process of claim 1 or 2 wherein all of said components sink or all of said components float.

5. The process of claim 1 or 2 wherein said carrier components are silicas, cellulose fibers, metal oxides, clays, infusorial earth, finely ground slag or lava, polyvinyl alcohol, polyvinyl alcohol copolymers, polyethylene oxide, hydroxypropyl methyl cellulose, paper, hydrophobic wood pin chips, cetyl alcohol, stearyl alcohol, vermiculite, ground cork, corn cob grits, bagasse, seed hulls, paper, particulate carbon materials, starches or modified starches, carrageenan, algin, xanthates, agar, or powdered polymeric materials, and combinations thereof.

6. The process of claim 1 or 2 wherein said carrier component is a hydrophobic or hydrophilic silica, a silicate, diatomaceous earth or sand.

7. The process of claim 1 or 2 wherein said carrier component is silica having a surface area of from about 50 to about 450 m²/g, an average agglomerate size of from about 3.5 to about 100 μm, or an average primary particle size of from about 12 to about 30 nm, a tapped density of from about 50 to about 240 g/l, a pH from about 3.6 to about 9 and a DBP (dibutyl phthalate) adsorption of from about 160 to about 335 g/100 g.

8. The process of claim 1 or 2 wherein said carrier component is a silicate having a surface area of from about 30 to about 40 m²/g, an average agglomerate size of from about 4 to about 6 μm, a tapped density of from about 285 to about 315 g/l, a pH of from about 9.5 to about 10.5 and a DBP adsorption of from about 150 to about 170 g/100 g.

9. The process of claim 1 or 2 wherein said coating component has a specific gravity greater than 1 or less than 1.

10. The process of claim 9 wherein said coating component has a specific gravity greater than 1 is, triethly citrate, acetyltriethyl citrate tri-n-butyl citrate acetyltri-n-butyl citrate acetyltri-n-hexyl citrate tri-n-hexytrimellitate, dicyclohexyl phthalate, diethyl phthalate, butyl phthalyl butyl glycolate, dimethyl isophthalate, or hydroxypropyl methyl cellulose, and combinations thereof.

11. The process of claim 9 wherein said coating component has a specific gravity less than 1 is n-butyryl-tri-n-hexyl citrate, monostearyl citrate, stearyl alcohol, cetyl alcohol, myristyl alcohol, octadecanoic acid, glyceryl stearate, or waxes, and combinations thereof.

12. The process of claim 1 or 2 wherein said bioactive agents are insecticides, toxicants, monomolecular surface films, petroleum oils, insect growth regulators, plant growth regulators, animal growth regulators, microbial control agents, pharmaceuticals, medicaments, antibiotics, pathogens, biological control agents, parasites, bactericides, viricides, fungicides, algaecides, herbicides, nematicides, amoebicides, miticides, acaricides, predicides, schistisomicides, molluscicides, larvicides, pupicides, ovicides, adulticides, nymphicides, attractants, repellents, growth stimulants, feeding stimulants, nutrients, hormones, chemosterilants, or pheromones, and combinations thereof.

13. The process of claim 1 or 2 wherein said bioactive agent is selected to treat mosquitoes.

14. The process of claim 13 wherein said bioactive agents are *Bacillus thuringiensis var. israeflensis, Bacillus sphaencus, Lagenidium giganteum,* methoprene, diflubenzuron, pyriproxyfen, temephos, chlorpyrifos, primiphos-methyl, lambda cyhalothrin, pyrethrins, 2 mol ethoxylate of isostearyl alcohol, lecithins, or petroleum oils, and combinations thereof.

15. The process of claim 1 or 2 wherein said bioactive agent is selected to treat aquatic plants.

16. The process of claim 15 wherein said bioactive agent is acrolein, aromatic solvents, water soluble copper compounds, dalapon, dichlorbenil, 2,4-D, diquat, endothall, glyphosate, simazine, and fluridone, and combinations thereof.

17. The process of claim 1 or 2 wherein said composition includes a binder.

18. The process of claim 17 wherein said binder is sulfonated polystyrene homopolymers, sulfonated styrene maleic anhydride polymers, sulfonated vinyl toluene maleic anhydride polymers, vinyl pyrrolidone polymers or copolymers, poly(isobutylene-co-disodium maleate) copolymers, acrylamide polymers or copolymers, acrylonitrile-starch graft polymers or copolymers, hydroxydropyl methyl cellulose, methyl cellulose, carboxymethyl cellulose polymers or copolymers, acrylate polymers or copolymers, poly(vinyl alcohol) polymers or copolymers, poly(ethylene oxide) polymers or copolymers, acrylic acid or acrylic ester homopolymers or copolymers, natural gums, synthetic gums, poly(ethylene glycol), clays, gypsum, plaster of paris, wax, paper, cellulose, latex, methyl vinyl ether maleic acid ester copolymers, starches or modified starches, and combinations thereof.

19. The process of claim 1 or 2, wherein said composition optionally includes a joint-function carrier/coating agent.

20. The process of claim 19 wherein said joint-function carrier/coating agent is polyvinyl alcohol, polyethylene oxide, hydroxypropyl methyl cellulose, cetyl alcohol or stearyl alcohol, and combinations thereof.

21. The process of claim 1 or 2 wherein said bioactive agent is B.t.i, methoprene, 2 mol ethoxylate of isostearyl alcohol, or the dipotassium salt of endothall, said coating is cetyl alcohol, triethyl citrate, acetyltriethyl citrate tributyl citrate, acetyltributyl citrate, acetyltri-n-hexyl citrate, n-butyltri-n-hexyl citrate, dicyclohexyl phthalate, butyl phthalyl butyl glycolate, tri-n-hexyl trimellitate, said carrier is hydrophobic silica, hydrophilic silica, hydrophobic wood pin chips, or sand, said composition includes as an optional binder, soluble starches or modified starches sulfonated polystyrene, a sulfonated vinylic polymer, an optional acrylic copolymer suspending agent, water soluble polyvinyl alcohol as an optional joint-function carrier/coating, and combinations thereof.

22. The process of claim 1 or 2 wherein said composition optionally includes at least one additional component to further regulate the controlled release rate and release profile of the bioactive agent in water wherein such components are diluents, adjuvants, dyes, alcohols, acetone, ketones, oils, surfactants, water, emulsifiers, film-forming agents, compatibility agents, wetting agents, salt, natural or synthetic polymers, hydrocolloids, buoyancy modifiers, ultraviolet absorbers, photo-protecting agents, suspending agents, elastomers, penetrants, deflocculating agents, dispersing agents, stabilizing agents, antifoaming agent sticking agents, solvents, co-solvents, catalysts, or synergists and combinations thereof.

23. The process of claim 1 wherein said composition is delivered as a liquid spray.

24. The process of claim 1 wherein said composition is delivered as a powder.

25. The process of claim 1 wherein said composition is delivered as an agglomerate.

26. The process of claim 1 wherein said composition is delivered from a degradable or soluble container.

27. The process of claim 1 wherein said composition is delivered from a container with at least one dispensing aperture.

28. The process of claims 1 or 2 wherein said coating also includes water soluble polyethylene oxide, hydroxypropyl methyl cellulose, methyl cellulose, or poly (vinyl alcohol) polymers or copolymers.

29. The process of claim 10 wherein said coating also includes water soluble polyethylene oxide, hydroxypropyl methyl cellulose, methyl cellulose or poly (vinyl alcohol) polymers or copolymers.

30. The process of claim 1 wherein said coating also includes water soluble polyethylene oxide, hydroxypropyl methyl cellulose, methyl cellulose, or poly (vinyl alcohol) polymers or copolymers.

31. The process of claim 1 or 2 wherein said bioactive agent is a pesticide.

32. The process of claim 1 or 2 where said coating component has a specific gravity of 1.

* * * * *

UNITED STATES PATENT AND TRADEMARK OFFICE
CERTIFICATE OF CORRECTION

PATENT NO.: 5,902,596

DATED: May 11, 1999

INVENTOR(S): Richard LEVY

It is certified that an error appears in the above-identified patent and that said Letters Patent is hereby corrected as shown below:

Claim 10, col. 37, lines 18-19, after "citrate" (each occurrence), insert --,--.

Claim 18, col 37, lines 61-62, "hydroxydropyl" should read --hydroxypropyl--.

Signed and Sealed this

Fourteenth Day of September, 1999

Attest:

Q. TODD DICKINSON

Attesting Officer

Acting Commissioner of Patents and Trademarks